United States Patent
Francischelli et al.

(10) Patent No.: US 7,347,858 B2
(45) Date of Patent: *Mar. 25, 2008

(54) METHOD AND SYSTEM FOR TREATMENT OF ATRIAL TACHYARRHYTHMIAS

(75) Inventors: David E. Francischelli, Anoka, MN (US); Scott E. Jahns, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 396 days.

This patent is subject to a terminal disclaimer.

(21) Appl. No.: 10/684,628

(22) Filed: Oct. 14, 2003

(65) Prior Publication Data

US 2004/0078069 A1    Apr. 22, 2004

Related U.S. Application Data

(63) Continuation of application No. 10/016,299, filed on Dec. 11, 2001, now Pat. No. 6,656,175.

(51) Int. Cl.
*A61B 18/18* (2006.01)
(52) U.S. Cl. .................................. 606/41; 128/898
(58) Field of Classification Search ............ 606/41–52; 128/898
See application file for complete search history.

(56) References Cited

U.S. PATENT DOCUMENTS

| | | |
|---|---|---|
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |

(Continued)

FOREIGN PATENT DOCUMENTS

EP    1075820 A1    2/2001

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner*—Scott M. Getzow
(74) *Attorney, Agent, or Firm*—Mike Jaro; Jeffrey J. Hohenshell

(57) ABSTRACT

A method and system for ablating tissue to provide a desired set of lesions. The system includes an ablation apparatus having an elongated shapeable section carrying a mechanism such as an electrode for applying ablation energy along the shapeable section. The shapeable section includes a member of shape memory material having a memorized configuration. The shapeable section is shaped manually or using fixtures to display a configuration corresponding to one of the desired lesions and is then employed to create the desired lesion. Thereafter the shapeable section is heated to cause it to resume its memorized configuration. Shaping, heating and ablating to create lesions are continued as necessary provide the desired set of lesions. In some embodiments of the invention, heating may be accomplished using heating elements built into the shapeable section.

26 Claims, 22 Drawing Sheets

U.S. PATENT DOCUMENTS

| | | |
|---|---|---|
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,147,355 A | 9/1992 | Friedman et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,357,956 A | 10/1994 | Nardella ............... 128/642 |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. ............... 128/642 |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Silwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. ............... 604/53 |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,596,995 A | 1/1997 | Sherman et al. ............ 128/736 |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |

| Patent | Date | Inventor |
|---|---|---|
| 5,681,308 A | 10/1997 | Edwards et al. |
| 5,685,878 A | 11/1997 | Falwell et al. ............... 606/49 |
| 5,687,723 A | 11/1997 | Avitall |
| 5,687,737 A | 11/1997 | Branham et al. |
| 5,688,267 A | 11/1997 | Panescu et al. ............... 606/41 |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. ................ 606/41 |
| 5,720,775 A | 2/1998 | Lanard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall ................... 606/23 |
| 5,735,280 A | 4/1998 | Sherman et al. |
| 5,735,290 A | 4/1998 | Sterman et al. |
| 5,755,760 A | 5/1998 | Maguire et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,871,523 A | 2/1999 | Fleischman et al. .......... 607/99 |
| 5,871,525 A | 2/1999 | Edwards et al. |
| 5,873,845 A | 2/1999 | Cline et al. |
| 5,876,399 A | 3/1999 | Chia et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,893,848 A | 4/1999 | Negus et al. |
| 5,895,417 A | 4/1999 | Pomeranz et al. .......... 607/101 |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,954,661 A | 9/1999 | Greenspon et al. |
| 5,971,980 A | 10/1999 | Sherman |
| 5,971,983 A | 10/1999 | Lesh |
| 5,993,447 A | 11/1999 | Blewett et al. |
| 6,007,499 A | 12/1999 | Martin et al. |
| 6,012,457 A | 1/2000 | Lesh |
| 6,016,811 A | 1/2000 | Knopp et al. |
| 6,032,077 A | 2/2000 | Pomeranz ................ 607/101 |
| 6,042,556 A | 3/2000 | Beach et al. |
| 6,045,550 A | 4/2000 | Simpson et al. ............ 606/42 |
| 6,063,081 A | 5/2000 | Mulier |
| 6,071,279 A | 6/2000 | Whayne et al. |
| 6,088,894 A | 7/2000 | Oakley |
| 6,096,037 A | 8/2000 | Mulier et al. ............... 606/49 |
| 6,113,592 A | 9/2000 | Taylor |
| 6,117,101 A | 9/2000 | Diederich et al. |
| 6,120,496 A | 9/2000 | Whayne et al. |
| 6,133,592 A | 10/2000 | Kishimoto et al. .......... 257/190 |
| 6,142,944 A | 11/2000 | Li et al. ................... 600/453 |
| 6,142,993 A | 11/2000 | Whayne et al. |
| 6,152,920 A | 11/2000 | Thompson et al. |
| 6,161,543 A | 12/2000 | Cox et al. .................. 128/898 |
| 6,165,174 A | 12/2000 | Jacobs et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,235,024 B1 | 5/2001 | Tu |
| 6,237,605 B1 | 5/2001 | Vaska et al. ................ 128/898 |
| 6,238,347 B1 | 5/2001 | Nix et al. |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,956 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,680 B1 | 12/2002 | Francischelli |
| 6,502,575 B1 | 1/2003 | Jacobs et al. |
| 6,514,250 B1 | 2/2003 | Jahns |
| 6,527,767 B2 | 3/2003 | Wang et al. |
| 6,537,248 B2 | 3/2003 | Mulier |

| | | | |
|---|---|---|---|
| 6,537,272 B2 | 3/2003 | Christopherson et al. |
| 6,558,382 B2 | 5/2003 | Jahns |
| 5,697,536 C1 | 6/2003 | Eggers et al. |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 2003/0045872 A1 | 3/2003 | Jacobs |
| 2003/0144656 A1 | 7/2003 | Ocel |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |

FOREIGN PATENT DOCUMENTS

| | | |
|---|---|---|
| WO | WO 99/59486 | 11/1999 |
| WO | WO 01/19269 | 9/2000 |
| WO | WO 01/72234 | 10/2001 |
| WO | WO 01/80724 | 11/2001 |

OTHER PUBLICATIONS

Gallagher et al., "Cryosurgical Ablation of Accessory Atriventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The Americal Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," *J of Thorac Cardiovasc Surg*,1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8½ Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

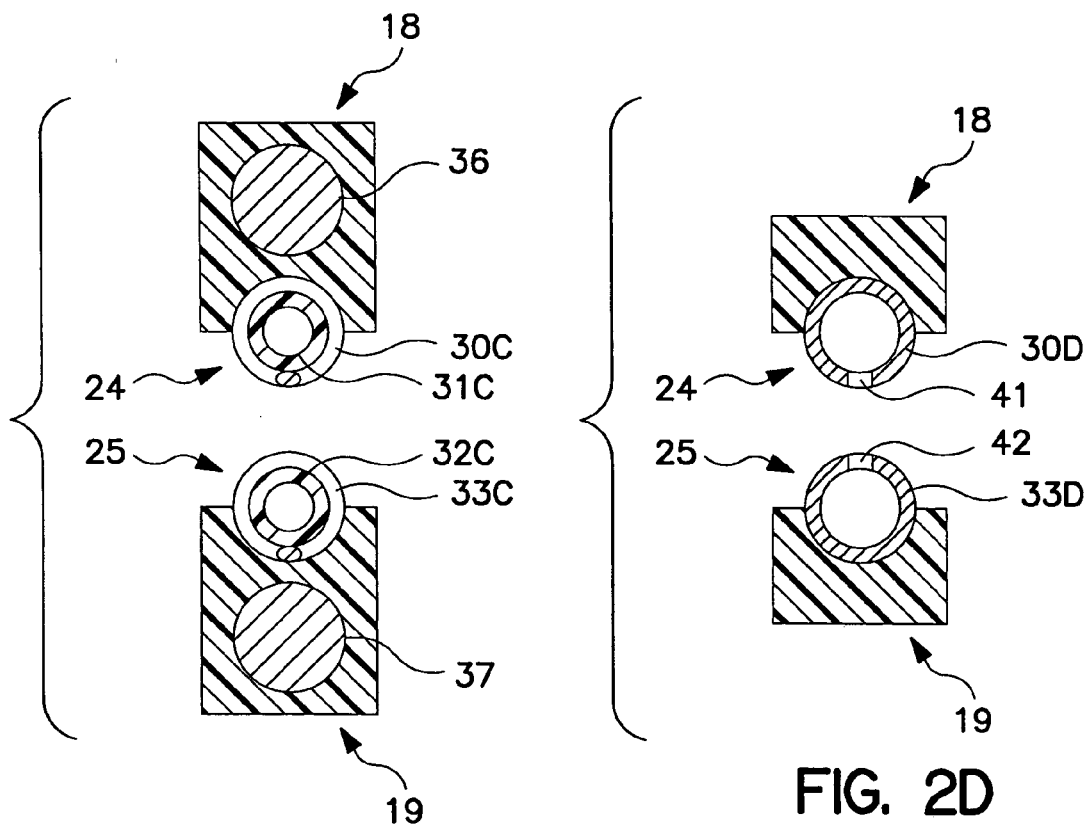
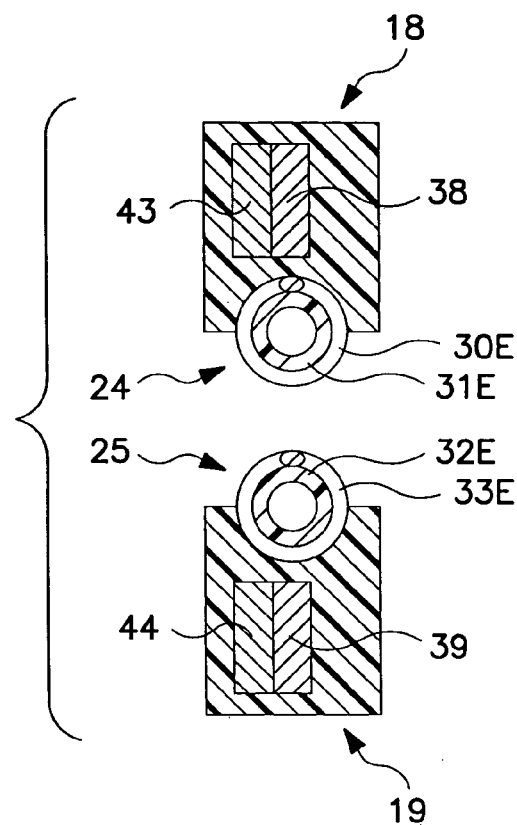
FIG. 2C
FIG. 2D
FIG. 2E

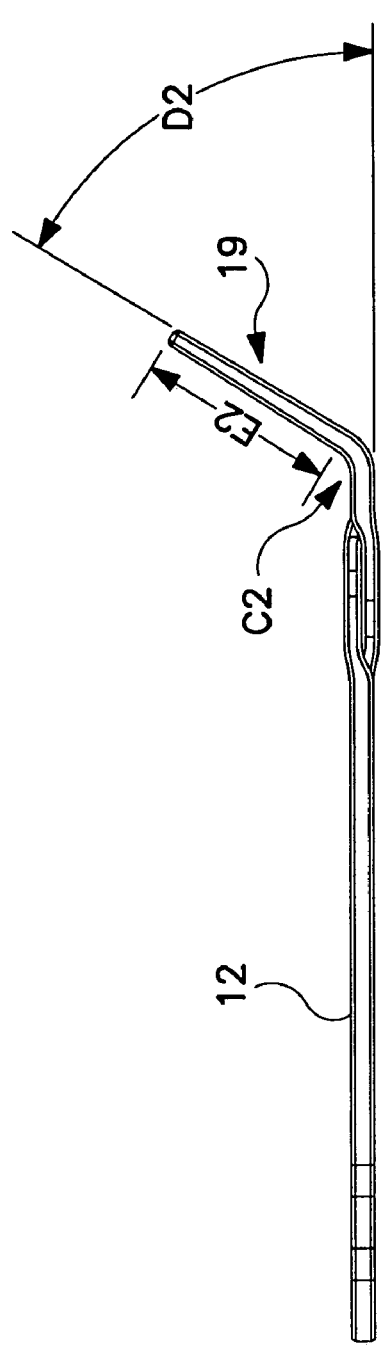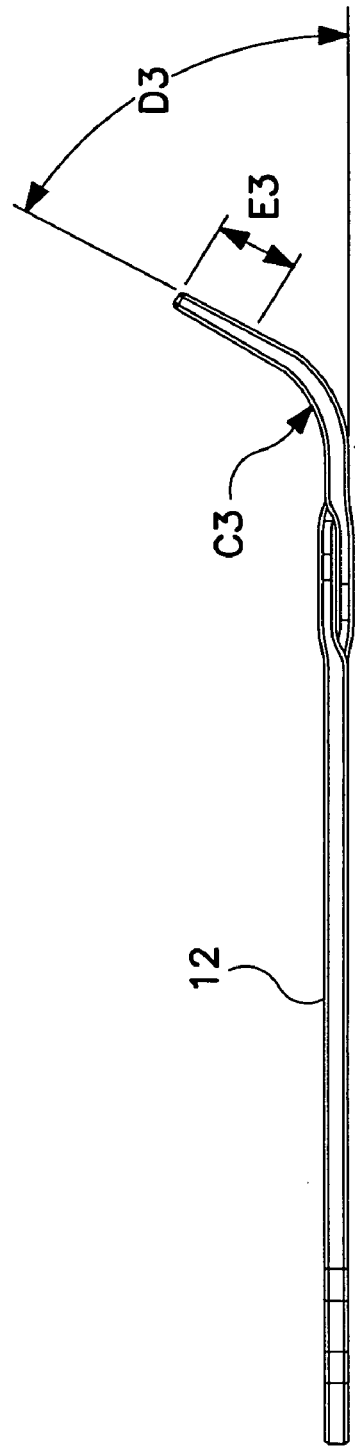

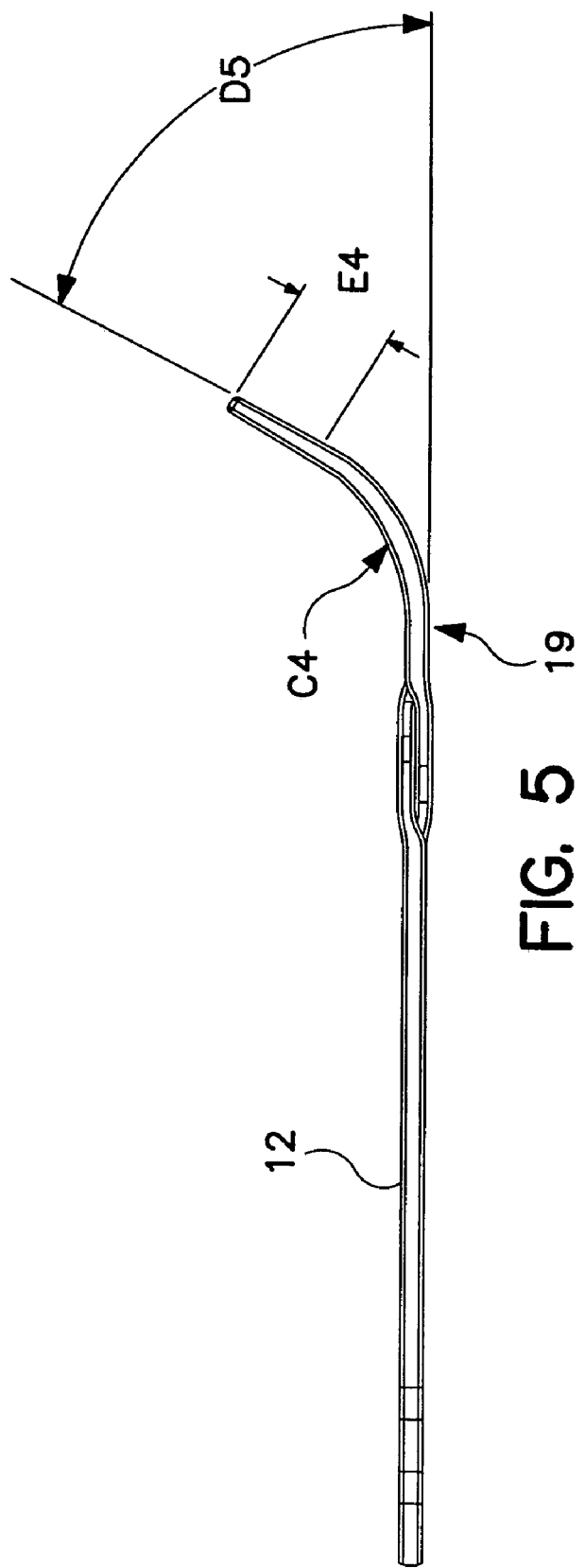

METHOD AND SYSTEM FOR TREATMENT OF ATRIAL TACHYARRHYTHMIAS

RELATED US APPLICATION DATA

This application claims priority as a continuation application from U.S. Ser. No. 10/016,299, filed Dec. 11, 2001, now U.S. Pat. No. 6,656,175.

BACKGROUND OF THE INVENTION

The present invention relates to surgical tools and procedures generally and relates more particularly to the use of ablation to create elongated lesions to treat atrial fibrillation or other medical conditions.

In patients with chronic atrial fibrillation having tachycardia that resistant to medical treatment, the Maze III procedure has been employed. This procedure controls propagation of the depolarization wavefronts in the right and left atria by means of surgical incisions through the walls of the right and left atria. The incisions create blind or dead end conduction pathways, which prevent re-entrant atrial tachycardias from occurring. While the Maze procedure is successful in treating atrial fibrillation, the procedure is quite complex and is currently practiced by only a few very skilled cardiac surgeons in conjunction with other open-heart procedures. The procedure also is quite traumatic to the heart, as in essence the right and left atria are cut into pieces and sewed back together, to define lines of lesion across which the depolarization wavefronts will not propagate.

It has been suggested that procedures similar to the Maze procedure could be instead performed by means of electrosurgical ablation, for example, by applying RF energy to internal or external surfaces of the atria to create lesions across which the depolarization wavefronts will not propagate. Such procedures are disclosed in U.S. Pat. No. 5,895,417, issued to Pomeranz, et al., U.S. Pat. No. 5,575,766, issued to Swartz, et al., U.S. Pat. No. 6,032,077, issued to Pomeranz, U.S. Pat. No. 6,142,944, issued to Swanson, et al. and U.S. Pat. No. 5,871,523, issued to Fleischman, et al, all incorporated herein by reference in their entireties. Hemostat type electrosurgical or cryo-ablation devices for use in performing such procedures are described in U.S. Pat. No. 5,733,280 issued to Avitall, U.S. Pat. No. 6,237,605 issued to Vaska, et al, U.S. Pat. No. 6,161,543, issued to Cox, et al., PCT published Application No. WO99/59486, by Wang and in pending U.S. patent application Ser. No. 09/747,609 filed Dec. 22, 2000 by Hooven, et al., all incorporated herein by reference in their entireties. In order for such procedures to be effective it is desirable that the electrosurgically created lesions are continuous along their length and extend completely through the tissue of the heart. In order for such procedures to be effective it is desirable that the electrosurgically created lesions are continuous along their length and extend completely through the tissue of the heart.

SUMMARY OF THE INVENTION

According to a preferred embodiment of the present invention, a maze type procedure may be performed using one or more bipolar electrosurgical hemostats, which apply ablation energy (e.g. RF energy) across the walls of the left and right atria by means of delivery means (e.g. electrodes) located on either side of the atrial walls. In a preferred embodiment of the invention, the hemostats are provided with elongated R-F electrodes capable of assuming various straight and curved configurations. In the particular embodiment of the invention described herein, a bipolar electrosurgical hemostat is provided, shapeable, for example, to a set of configurations adapted to allow the physician to approximate the incisions that would occur during the Maze III procedure as described in the book '*Cardiac Surgery Operative Technique*' by Donald B. Doty, M.D. at pages 410-419, incorporated herein by reference in its entirety, and herafter referred to as the "Doty reference". Other curved configurations may also be accomplished, using the shapeable hemostat of the present invention, to allow approximation of the incisions that would be provided by other forms of the Maze procedure or to perform other ablation procedures.

The shapeable hemostat according to a preferred embodiment of the present invention is provided with elongated jaws that carry electrodes or other means for applying ablation energy to a patent's heart. The jaws of the hemostat may each carry a single, elongated electrode or may each carry a series of electrodes. While the preferred embodiment of the invention as disclosed takes the form of a hemostat with R-F electrodes extending along both jaws, it is believed the invention may also usefully be practiced in a device having only a single elongated shapeable electrode or series of electrodes, for application of ablation energy to only the inner or outer surface of the wall of a heart chamber.

The jaws are fabricated of or provided with a core formed of a shape memory material, e.g. a nickel titanium alloy such as Nitinol, a copper-nicel aluminum or copper zinc aluminum alloy (SME brass) or a plastic having shape memory properties. If the shape memory material is not itself biocompatble, it should be encased in a biocompatible covering, e.g. encapsulated within the material of the jaws. The material chosen preferably displays its memorized configuration at a temperature above the temperature to which it will be heated during the ablation procedure. This temperature will be dependant on the construction of the jaws of the hemostat, and will vary depending on the degree of thermal insulation between the electrode and the shape memory material. If the electrode itself is the shape memory component, then the transition temperature should be above 50 degrees Celsius. In any case, the transition temperature should be well above body temperature. The transition temperature should be below the temperature to which it will be heated to resume its memorized configuration, e.g. less than 100 degrees Celsius, if heated using boiling water, above 100 degrees Celsius if placed in a heater. The specific composition of the alloy or plastic material can be chosen to control transition temperature, using standard techniques. The jaws of the hemostat may thereby be shaped at room temperature and will retain their shape during subsequent use in the body to ablate tissue. The memorized configuration may be straight or curved.

In use, the jaws of the hemostat are shaped manually or with the use of a bending fixture to exhibit a desired configuration for use in producing a particular lesion. As noted above, these lesions may be produced as part of a procedure corresponding to a Maze type procedure. After the lesion is produced, the shape memory material in the jaws of the hemostat is heated to a temperature above its transition temperature so that the jaws return to their memorized configuration and may then either be used in this configuration to produce the next lesion or may be again shaped to an alternative desired configuration. This process is continued until all desired lesions have been produced. Because the jaws are returned to their memorized configuration, e.g. straight, before reshaping, any kinks or curves resulting from the previous reshaping will be eliminated. This allows the jaws to be successively reshaped, with subsequent reshapings unaffected by previous reshapings.

The jaws may be heated by any convenient means, for example by placement in hot water, placement in or on an electric heater, or by means of resistive heaters built into the jaws themselves. The configurations assumable by the hemostat jaws may be straight, curved or bent, adapted to an individual patient according to the judgment of the physician. Alternatively, the physician may be provided with a set of bending fixtures to provide a pre-determined set of curved configurations, each configuration associated with one or more of a predetermined set of desired lesions.

The particular embodiment of the invention as disclosed herein is described in the context of hemostats particularly adapted for treatment of atrial fibrillation during open chest surgery, with the patient undergoing cardiopulmonary bypass. However, the present invention is also believed applicable to closed chest procedures, in which the heart is observed thoracoscopically and access is provided by means of thoracoscopic surgical ports. It is believed the invention is also applicable to other procedures involving creation of a set of elongated lesions in heart tissue or elsewhere in the body.

A BRIEF DESCRIPTION OF THE DRAWINGS

Figure 1A:
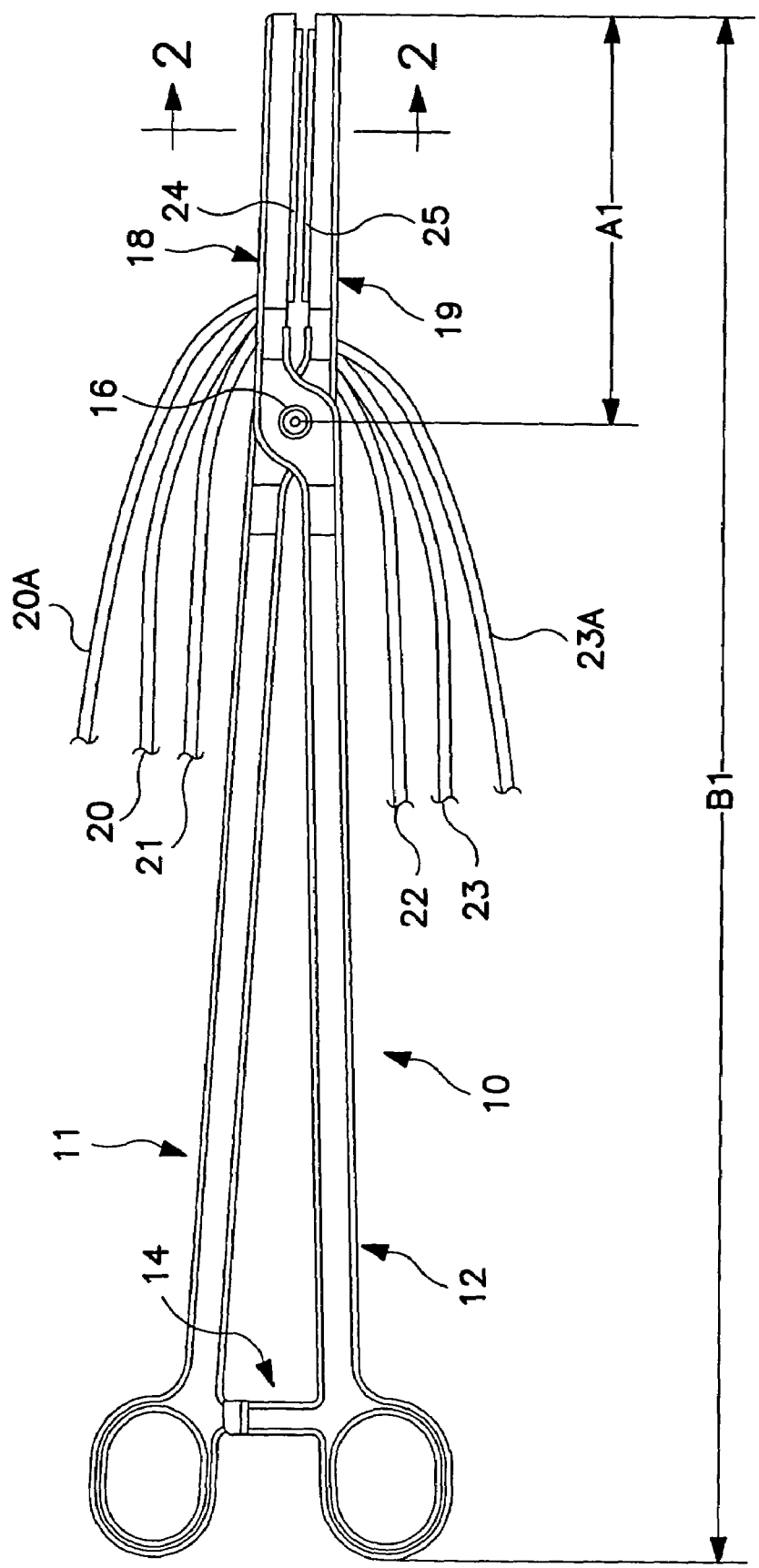
FIG. 1A illustrates an electrosurgical hemostat according to the present invention having two elongated jaws that exhibit a memorized, generally straight configuration.

FIGS. 2A, 2B, 2C, 2D and 2E all illustrate cross section through alternative embodiments for the jaws of the hemostat otherwise as illustrated in FIG. 1A.

FIG. 3 illustrates a side view of an electrosurgical hemostat according to the present invention, shaped to display a bent configuration.

FIG. 4 illustrates a side view of an electrosurgical hemostat according to the present invention, shaped to display a first, curved configuration.

FIG. 5 illustrates a side view of an electrosurgical hemostat according to the present invention, shaped to display a second, curved configuration.

Figure 6A:
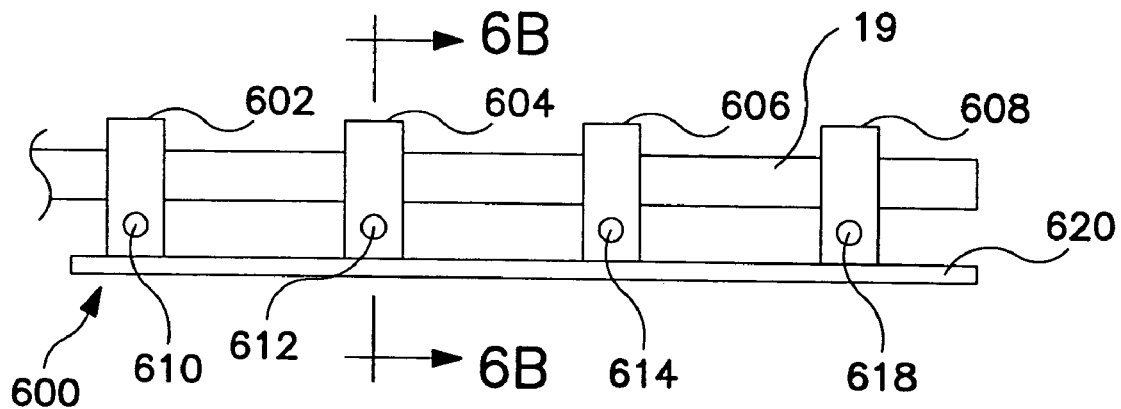
Figure 6B:
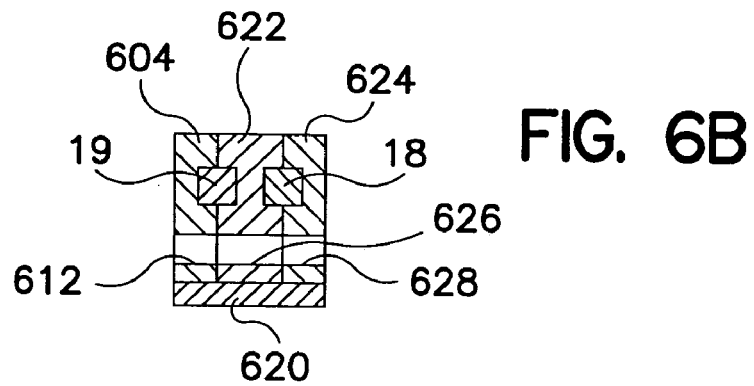
Figure 6C:
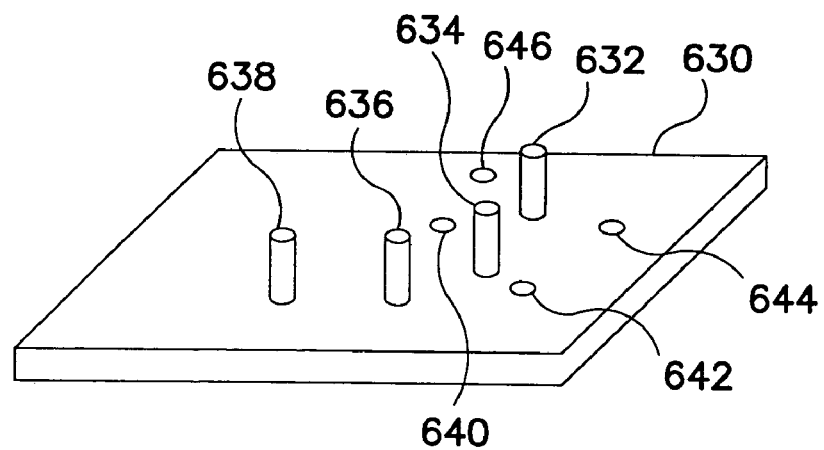

FIGS. 6A, 6B and 6C illustrate operation of a first bending fixture according to the present invention.

Figure 7A:
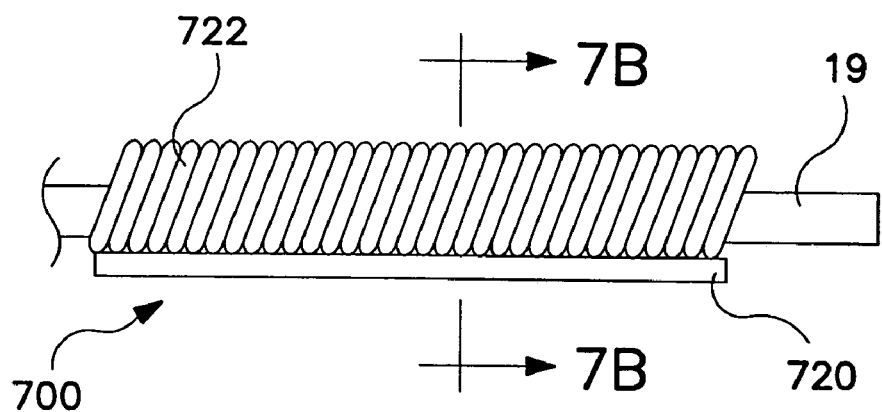
Figure 7B:
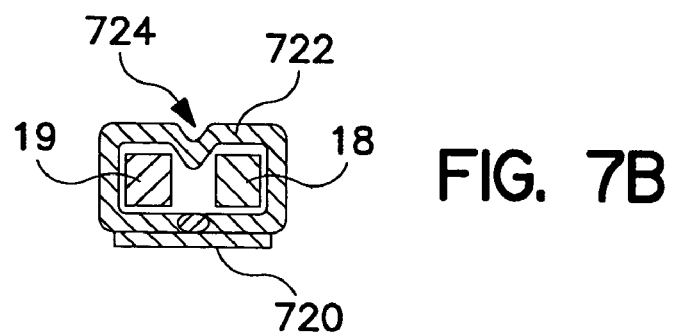
Figure 7C:
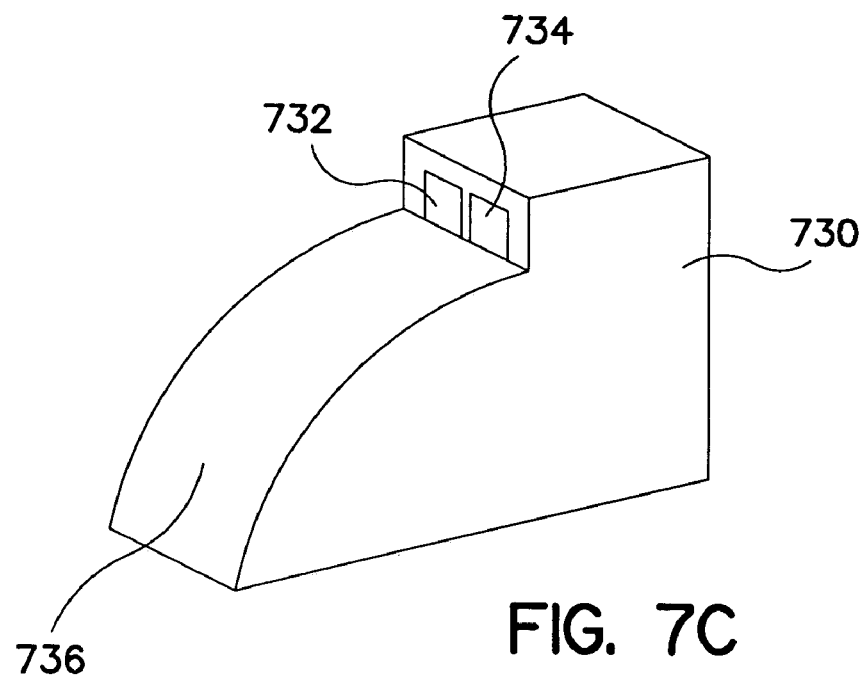

FIGS. 7A, 7B and 7C illustrate operation of a second bending fixture according to the present invention.

Figure 8A:
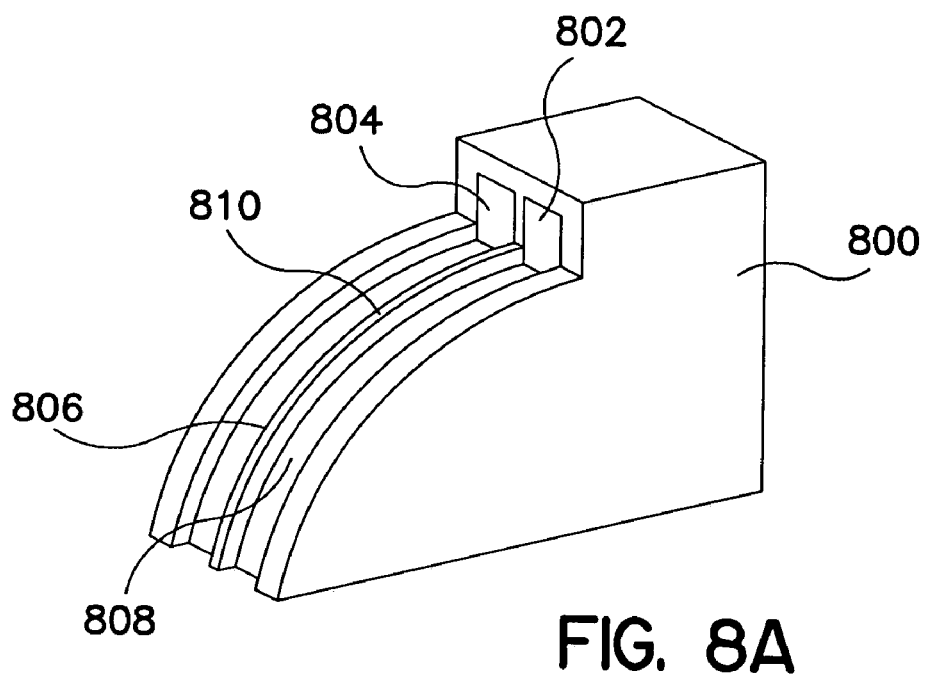
Figure 8B:
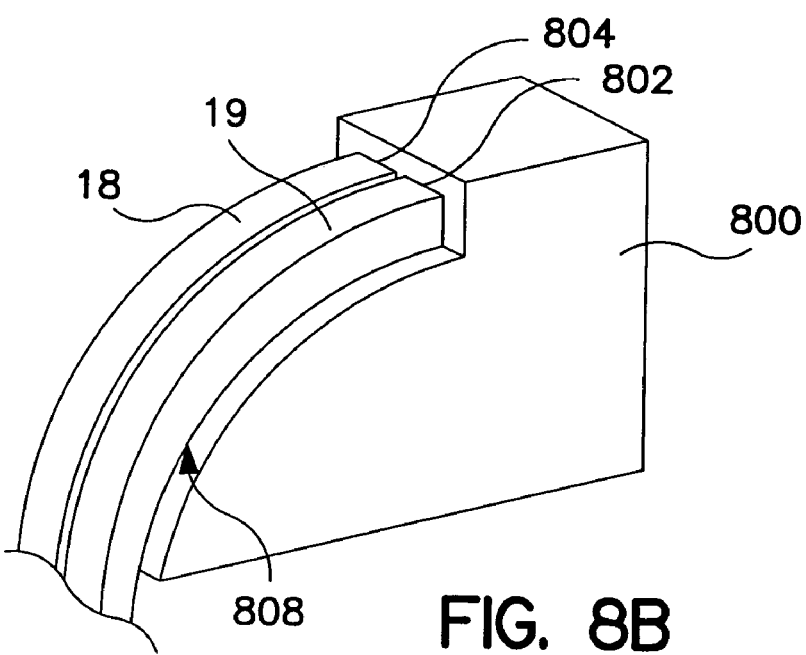

FIGS. 8A and 8B illustrate operation of a third bending fixture according to the present invention.

FIGS. 9A through 9M are a series of drawings illustrating schematically a surgical procedure performed using an electrosurgical hemostat according to the present invention and illustrating schematically the various incisions and lesions produced.

DETAILED DESCRIPTION OF THE PREFERRED EMBODIMENTS

The embodiment of the invention as disclosed in the present application includes a shapeable electrosurgical hemostat and mechanisms for causing the jaws of the hemostat to assume predetermined configurations particularly adapted to perform an ablation procedure modeled on the Maze III procedure as described in the Doty reference, cited above. Within the context of the invention, however, other predetermined sets of configurations may be substituted and/or the physician may simply manually shape the jaws of the electrodes to his liking. The set of configurations is described in more detail below.

FIG. 1A illustrates a top plan view of a hemostat provided according to the present invention. The hemostat may be approximately 31 centimeters in overall length as illustrated at B2, with jaws of approximately 8 centimeters in length, as illustrated at A1. The hemostat includes two elongated handle members 12 and 14, each provided with a finger loop at its proximal end. A conventional hemostat locking mechanism 14 is also provided. The handles of the hemostat may be fabricated of stainless steel or other readily resterilizable material. Alternatively, the handles 11 and 12 might be fabricated of a biocompatible plastic and/or the hemostat may be disposable.

To the jaws 18 and 19 of the hemostat extend distally from the pivot or hinge 16, and carry elongated electrosurgical electrodes 24 and 25. When the jaws are parallel to one another, electrodes 25 and 25 are preferably spaced approximately 0 to 7 mm from one another, more preferably 1 to 5 from one another, to facilitate uniform contact along opposite sides of a patient's atrial wall. In use, the atrial wall is compressed between electrodes 24 and 25, and R-F energy is applied between the electrodes in order to create an elongated continuous lesion extending through the cardiac tissue.

Using the hemostat as configured in FIG. 1A, a linear lesion is produced. I the particular embodiment illustrated, the jaws exhibit a memorized, generally straight configuration.

The electrodes 24 and 25 are preferably configured to allow fluid—assisted cardiac ablation, of the type generally described in U.S. Pat. No. 6,096,037 issued to Mulier, incorporated herein by reference in its entirety. To this end, each of the electrodes is provided with an electrical conductor, 20, 23, allowing delivery of R-F electrical energy to the electrodes 24 and 25, respectively and with a fluid lumen 21, 22, allowing for delivery of saline solution or other conductive fluid to and along the length of electrodes 24 and 25. If resistive heaters are included, arranged along the length of the jaws 18, 19, additional conductors 20A and 23A are provided in order to power the heaters. Various alternative embodiments of the electrodes and jaws of the hemostat of FIG. 1A are illustrated in FIGS. 2A through 2D, discussed below.

In use in a preferred embodiment of the invention, one jaw of the hemostat of FIG. 1A is inserted into the interior right or left atrium through an incision provided in the wall of the left or right atrium, while the other jaw remains outside of that chamber. The jaws are pressed together, somewhat compressing the atrial wall between the jaws, to provide for continuous contact along the length of the jaws on both sides of the atrial wall. The ablation jaws in some cases may instead be arranged along opposing external surfaces of an organ, for example opposite sides of an atrial appendage or along opposite sides of the tissue adjacent the bases of the right or left pulmonary veins.

RF energy is delivered between the electrodes. Delivery of energy or power to assure a complete lesion may be accomplished by measurement of impedance between the electrodes, as in U.S. Pat. No. 6,133,592, issued to Taylor, U.S. Pat. No. 5,718,701, issued to Shai, et al or U.S. Pat. No. 5,357,956, issued to Nardella, or allowed Pending U.S. application Ser. No. 09/347,635, filed Jul. 6, 1999 by Hoey et al, all incorporated herein by reference in their entireties. Alternatively, thermocouples or other temperature sensors may be added to the jaws of the hemostat and delivery of energy or power controlled as in U.S. Pat. No. 5,685,878, issued to—Falwell, et al., U.S. Pat. No. 6,045,550, issued to Simpson, et al., U.S. Pat. No. 5,688,267, issued to Panescu, et al or U.S. Pat. No. 5,596,995, issued to Sherman, et al., all also incorporated herein by reference in their entireties. As an additional alternative, delivery of energy or power may be time terminated, based upon empirically determined times found to lesions extending completely through the atrial walls at the power or energy levels chosen, or regulation of ablation energy by means of any of the references cited above may be employed if appropriate.

Figure 1B:
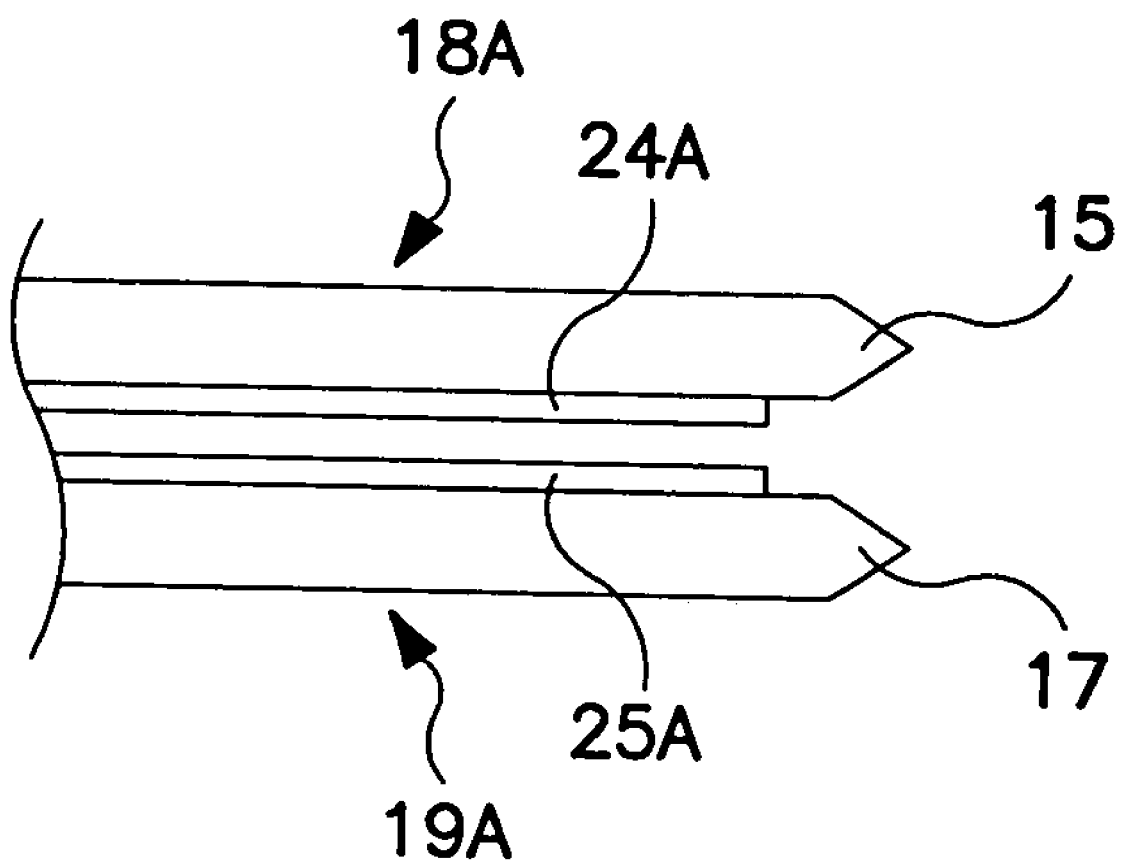
FIG. 1B illustrates an alternative configuration for the tips of the jaws of the hemostat illustrated in FIG. 1A.

It is anticipated that in some versions of the present invention which employ a more limited access approach to the heart, the distal tips of hemostat jaws themselves may be sharpened and used to pierce the atrial wall, eliminating the necessity of a separate incision. FIG. 1B illustrates such an alternative hemostat jaw construction, wherein hemostat jaws 18A and 19A correspond generally to jaws 18 and 19 in FIG. 1A, and carry electrodes 24A and 25A which also correspond to electrodes 24 and 25 in FIG. 1A. However, the distal tips 15 and 17 of the jaws are sharpened to a point or an edge so that either may be used to directly penetrate the atrial wall, eliminating the necessity of a separate incision.

Figure 2A:
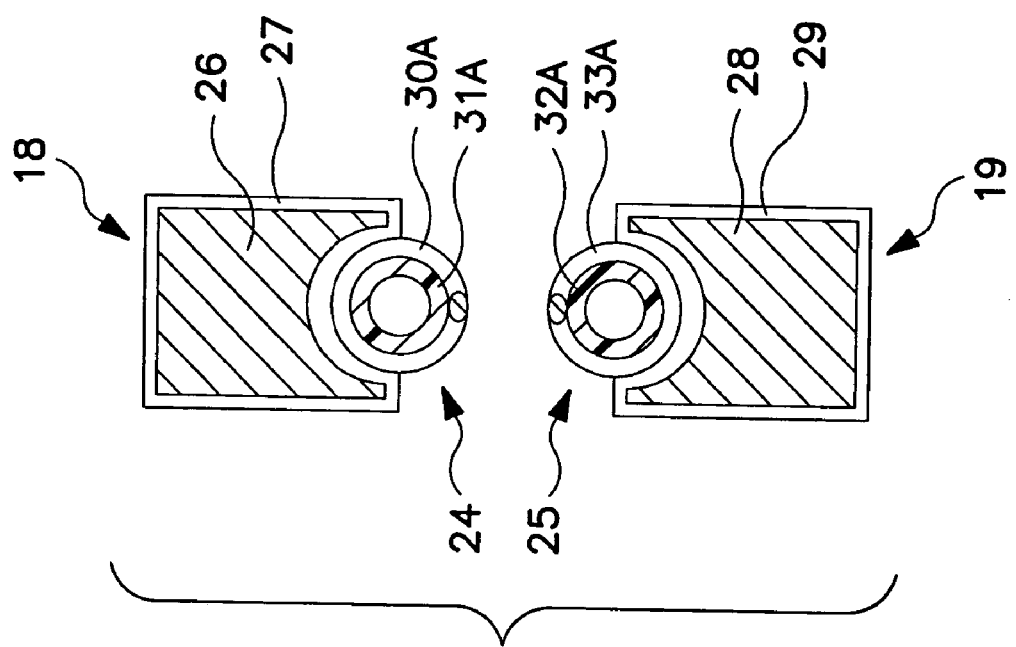

FIGS. 2A through 2E are cross sectional views through the jaws of a hemostat as in FIG. 1A, illustrating possible alternative constructions. In FIG. 2A, the jaws 18 and 19 are made of metallic cores 26, 28, of shape memory metal such as Nitinol, covered by insulative coatings or paint, 27, 29. Resistive heaters 34 and 35 are optionally provided, extending along the cores 26, 28. Electrodes 24 and 25 take the form of elongated conductive coils, 30A, 33A, carrying tubes 31A, 32A, of expanded PTFE, through which a conducted fluid such as saline solution may be delivered along the length of the electrode coils 30A, 33A. The lumens of the EPTFE tubes 31A, 32A may be sealed at their distal extremities.

Figure 2B:
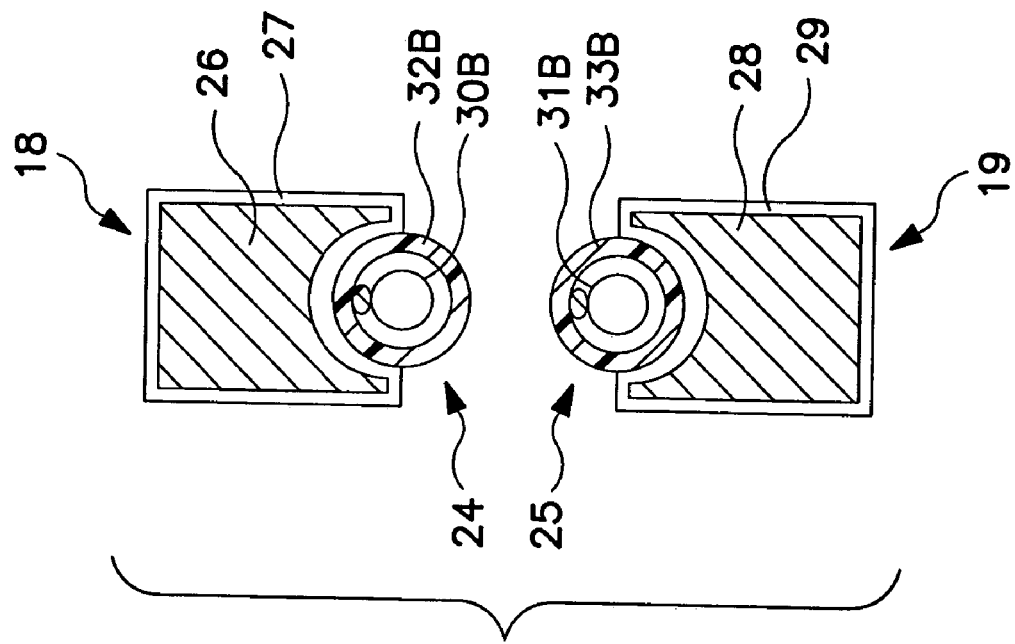

FIG. 2B illustrates a first alternative embodiment, corresponding generally to that illustrated in FIG. 2A, with identically numbered elements corresponding to those illustrated in 2A. In this embodiment, the configuration of the conductive coil, 31B, 32B and the expanded PTFE tubes, 32B, 33B is reversed, so that the coils are located within the EPTFE tubes. As in the embodiment illustrated in FIG. 2A, saline or other conducted fluid is delivered through the inner lumen of EPTFE tubes 32B, 33B. Resistive heaters are not included, so heating of the hemostat to resume its memorized configuration must be accomplished using other means, such as placing the jaws of the hemostat in a vessel filled with hot water, or into or on an electric heater.

FIG. 2C illustrates a third embodiment according to the present invention. In this case, elements correspond to identically numbered elements in FIG. 2A. However, in the embodiment of FIG. 2C, the jaws 18, 19, take the form of molded plastic members with cores formed of shape memory metal rods 36, 37.

FIG. 2D illustrates a fourth embodiment according to the present invention. Elements correspond to identically labeled elements in FIG. 2A. In this embodiment, the jaws 18, 19 are molded plastic members and the electrodes 24, 25 take the form of tubes of shape memory metal, provided with a series of holes 41, 42, open to the lumen of the tube. In this embodiment, conductive fluid is delivered through the lumen of the tube and to the tissue through the holes 41, 42, and no separate fluid delivery tube is required.

FIG. 2E illustrates a fifth embodiment according to the present invention. Elements correspond to identically labeled elements in FIG. 2A. However, in the embodiment of FIG. 2E, the jaws 18, 19, take the form of molded plastic members with cores 38, 39, formed of shape memory metal. Cores 38 and 39 are rectangular in cross section, encouraging bending of the jaws in parallel planes. This feature may be particularly desirable if bending of the jaws manually, without bending fixtures, is to be performed.

FIGS. 3-5 illustrate various curved and bent configurations of the hemostat of FIG. 1A, adapted to perform an ablation procedure analogous to the Maze III procedure. While electrodes are not illustrated in these figures, they should be understood to be present and to correspond with those illustrated in FIGS. 2A-2E. Similarly, While conductors and fluid lumens are not illustrated in FIGS. 3-5, they should be understood to be present and correspond to those as illustrated in FIG. 1A.

FIG. 3 illustrates a side view of the hemostat of FIG. 1A wherein the jaws 18 and 19 are shaped to describe a generally straight distal portion extending over a length E2, which may be, for example, 5½ centimeters. The jaws are bent at C2 around a radius of approximately 0.5 centimeters and describe an angle D2 of approximately 60 degrees, as illustrated.

FIG. 4 illustrates a side view of the hemostat of FIG. 1A wherein the jaws 18 and 19 are shaped to define a distal, generally straight portion E3 extending for approximately 2 centimeters, and are curved around a radius C3 of approximately 3 centimeters, to define an angle D3 of approximately 65 degrees.

FIG. 5 illustrates a side view of the hemostat of FIG. 1A wherein the jaws 18 and 19 are shaped to define a generally straight distal portion extending over a length E4 of approximately 3 centimeters, and curved around a radius C4 of approximately 5 centimeters to define an angle D5 of approximately 60 degrees.

FIGS. 6A, B & C illustrate a first fixturing system for bending jaws of a hemostat as illustrated in FIG. 1A to assume a desired curved configuration. The apparatus illustrated in FIGS. 6A through 6C is intended to assure that the jaws assume the desired curved configurations and that they also remain parallel to one another, facilitating their use to provide bipolar ablation along the entire length of the electrodes on the jaws.

FIG. 6A shows the first component 600 of the fixturing system in side view, with jaw 19 of the hemostat of FIG. 1A visible mounted within the component. The component includes a flexible backbone 620, for example, fabricated of spring steel, to which a series of upwardly extending members 602, 604, 606, 608 are mounted. Each of these members, 602, 604, 606 and 608 is one of a set of three members arranged to engage both jaws of the hemostat and retain them in a parallel configuration. Each of the members is provided with a hole 610, 612, 614 for engaging a pin on the second component of the fixturing system, discussed below in conjunction with FIG. 6C.

FIG. 6B illustrates a cross-sectional view through the first component 600 of the fixturing system illustrating upwardly extending member 604 and its corresponding associated upwardly extending members 622 and 624. Members 604, 622 and 624 together define two openings, which receive the jaws 18 and 19 of the hemostat as illustrated. Members 604, 622, 624 may be spread apart from one another slightly, due to the resilience of the base member 620, to allow insertion of the jaws 18 and 19 of the hemostat. Members 622 and 624 are provided with holes, 626 and 628, aligned with hole 612 in member 604.

FIG. 6C illustrates the second component of the fixturing system, comprising a metal plate 630 having a plurality of holes arranged corresponding to desired curved configurations to be displayed by the hemostat jaws. As illustrated, pins 632, 634, 636, and 638 are inserted in one set of holes to define a first curved configuration. Unused holes 640, 642, and 646 are employed to create alternative curved configurations.

In use, the first component 600 of the fixturing system, mounted to the jaws 18 and 19 of the hemostat is fitted to the second component 630 by bending the jaws of the hemostat so that the pins 632, 634, 636 and 638 pass through the holes defined in the upwardly extending members, assuring the displayed curvature of the hemostat is as desired.

The hemostat is then removed from the fixturing member and employed to create a lesion having a configuration corresponding to the provided curvature. After creation of the lesion, if the configuration of the hemostat is to be altered before the next lesion is produced, it is heated to cause it to resume its original memorized configuration, for example, a straight configuration as illustrated in FIG. 1A. The hemostat may be used to create a lesion in this configuration or may be reshaped to display a different curved configuration using the fixture system.

The advantage of the step of heating the hemostat jaws to assume their previous memorized confirmation as opposed to simply re-bending the jaws to assume a second curved configuration is that it eliminates any set bends or kinks that might interfere with the jaws assuming their desired new configuration. For example, if the jaws have been shaped to provide the sharply bent configuration illustrated in FIG. 3, re-bending the jaws to assume a smoothly curved configuration as in FIGS. 4 and 5 would otherwise be difficult in view of the tendency to the jaws to retain the small radius bend as illustrated in FIG. 3. Similarly, returning the jaws to a straight configuration simply by attempting to re-bend the jaws may be difficult due to the tendency of the jaws to retain their previously imparted curved configuration.

FIGS. 7A through 7C illustrate a second fixturing system which may be used to impart desired predefined curves or may be used to assist the physician in providing manually shaped curves while retaining the jaws of the hemostat in a parallel configuration. The fixturing system of FIGS. 7A through 7C includes a first component 700 as illustrated in FIG. 7A. This first component includes a flexible base member 720, which may be fabricated of spring steel or other flexible material having a strong tendency to bend only in a single plane. Attached to base member 720 is a coil 722 having an interior lumen specifically configured to receive the two jaws 18 and 19 of the hemostat. As illustrated, jaw 19 as visible inserted into the coil 722.

FIG. 7B illustrates the first component of the fixturing system in cross section. In this view it can be seen that the coil 722 provides a generally rectangular internal lumen in which the jaws 18 and 19 of the hemostat are mounted. Individual coils are provided with a depression 724 which defines the desired spacing between the jaws during the bending operation. With this fixture attached to the jaws, the physician may bend the jaws manually, assuring that they remain in a parallel configuration. After bending, the first component of the fixture is simply removed from the jaws by sliding it off the distal ends of the jaws.

Alternatively, the first component 700 may be used in conjunction with a second fixturing component 730 to provide a predefined curve. Fixturing component 730 is provided with two generally straight recesses 732 which have a depth adapted to provide any desired straight distal portion of the jaws as configured. For example, the depths of the recesses 732 and 734 may correspond to lengths of the straight portions E2, E3, or E4, as illustrated in FIGS. 3, 4 and 5 respectively. The second component 730 of the fixturing system includes a defined curved surface 736, around which the first fixturing component 700, carrying the jaws 18 and 19 of the hemostat, is bent to provide a defined curvature corresponding to the curvature of the surface 736.

In this fixturing system, it is envisioned that several components to similar to component 730, each having a different defined curved surface and recesses of differing depths for receiving the distal ends of the hemostat jaws may be provided to provide a family of desired curved configurations.

FIGS. 8A and 8B illustrate a third fixturing system, employing fixturing components similar to fixturing components 730, illustrated in FIG. 7C. In this system, however, no restraining devices are mounted to the jaws of the hemostat to be reshaped, simplifying the process. Fixturing component 800 is provided with two inwardly extending recesses 802 and 804, corresponding generally to recesses 732 and 734 in the fixturing component illustrated in FIG. 7C. In a similar fashion, they are provided with a depth that corresponds to the length of any straight, distal portion desired for the jaws. In addition, the component 800 is provided with two grooves 806 and 808, extending along a desired curvature for the hemostat. A raised portion 810 separates the grooves and defines the desired inter-jaw spacing during the bending operation. The combination of the recesses 802, 804, the grooves 806 and 808 and the raised portion 810 provide a mechanism for retaining the jaws in a parallel configuration while bending them to assume the desired curvature.

FIG. 8B illustrates the jaws 18 and 19 of the hemostat inserted into the recesses 802 and 804 of the fixturing component 800, and bent around the component, arranged within the grooves 806 and 808. After bending, the hemostat is simply removed from the fixturing component 800 and may be employed to create the lesion having a configuration corresponding to the curvature provided by the fixturing component 800. In this embodiment of the invention, a set of components similar to fixturing 800 would be provided, each having recesses of a desired depth to define any straight distal portion of the jaws, and having grooves extending around a predefined desired curvature to define the curved portion of the jaws.

In the discussion of the various bending and fixturing systems above, it is assumed that the memorized configuration of the hemostat jaws is a straight configuration. In conjunction with the procedure defined below, as many of the lesions are performed using the jaws in this straight configuration, this is probably the most desirable embodiment. However, in other procedures, it may be desirable to employ a memorized configuration that has a preset curve, if this curved configuration is used for a substantial portion of the lesions to be performed. In this case, the fixturing devices as illustrated in FIGS. 6A-8B may be modified to provide a mechanism for bending the hemostat jaws to assume a straight configuration. In all of the embodiments in FIGS. 6A through 8B, it should be understood that the curvature defined by the fixturing mechanism is preferably is somewhat greater than the ultimately desired curvature, due to the fact that some elastic rebound of the hemostat jaws after bending is to be expected. As such, each fixture must be designed to provide for some degree of over-bending as compared to the desired ultimate configuration. A specific degree of over-bending provided by any particular fixture will, of course, be a function of the specific shape memory material chosen and of the specific configuration of the shape memory material.

It should also be noted that in the above discussion of the procedures associated with heating the forceps to allow them to assume their memorized condition, the heating step is generally conceived of as occurring external to the body, as a relatively elevated temperature may be generally be required. However, in some cases, it is possible that the step of heating the forceps jaws might occur internal to the patient's body, for example, in those embodiments in which resistive heaters are provided, extending along the jaws. In these cases, it is envisioned that the hemostat might remain within the patient's body while electrical power is applied to cause the resistive heaters to in turn cause the hemostats to resume to their memorized straight or curved configurations.

FIGS. 9A-9M are schematic drawings which illustrate a procedure performed using the bipolar electrosurgical hemostats described above to obtain a result analogous to the Maze III procedure as described in the Doty reference cited above. The lesions produced using the hemostats correspond to incisions as described in this reference, and the correspondence of the lesions to the incisions is described below.

Figure 9A:
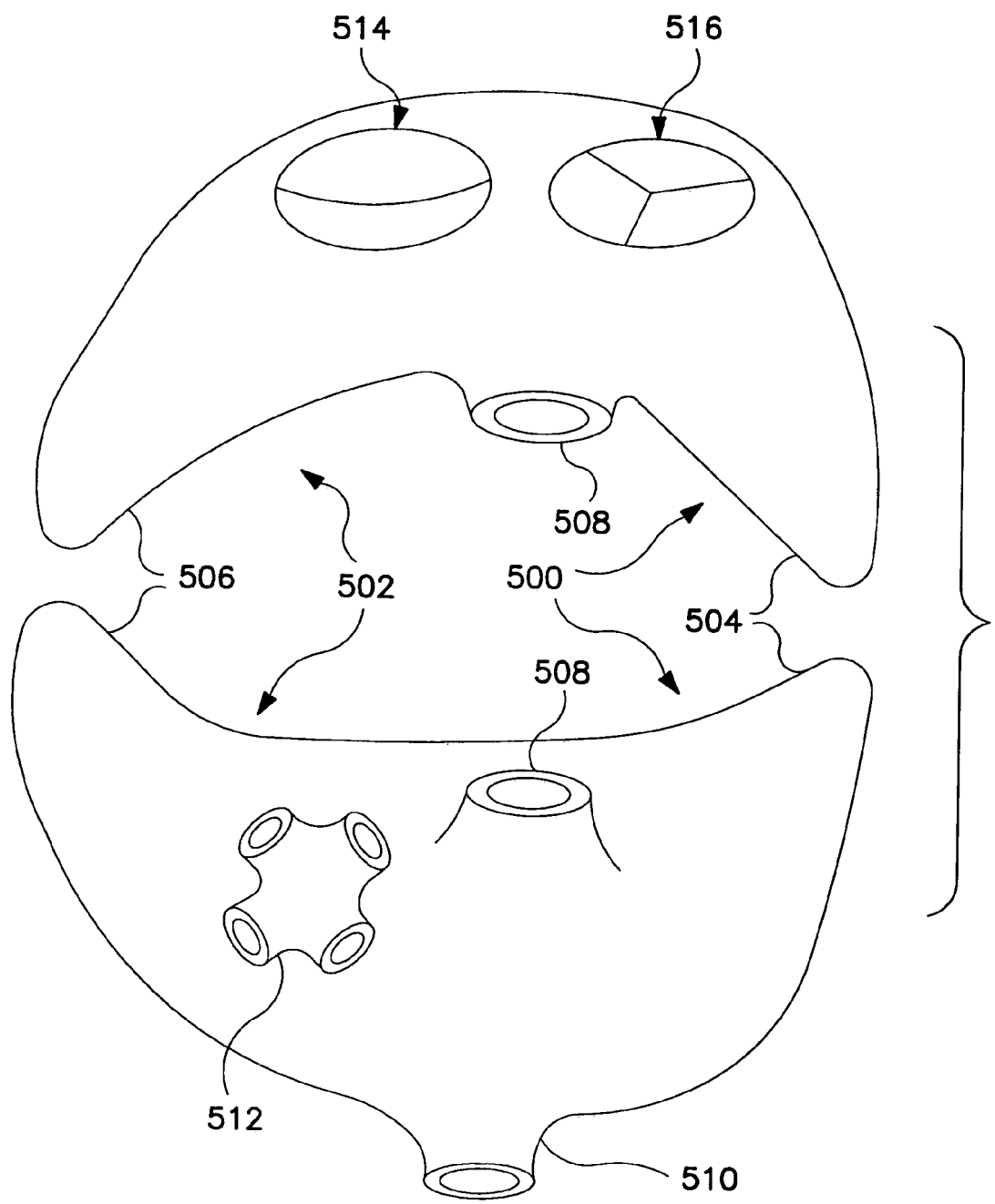

FIG. 9A is a schematic drawing illustrating the structure of the right and left atria, 500, 502, respectively, as viewed from a lower aspect, including tricuspid valve 16 and mitral valve 14 and as viewed from a more superior aspect, including the bases of the pulmonary veins 512 and the bases of the superior vena cava and inferior vena cava, 508 and 510 respectively, which enter the right atrium 500. The right and left atrial appendages are also illustrated schematically at 504 and 506, respectively. The structures as illustrated in FIG. 9A are correspondingly numbered in FIGS. 9B-9M below.

Figure 9B:
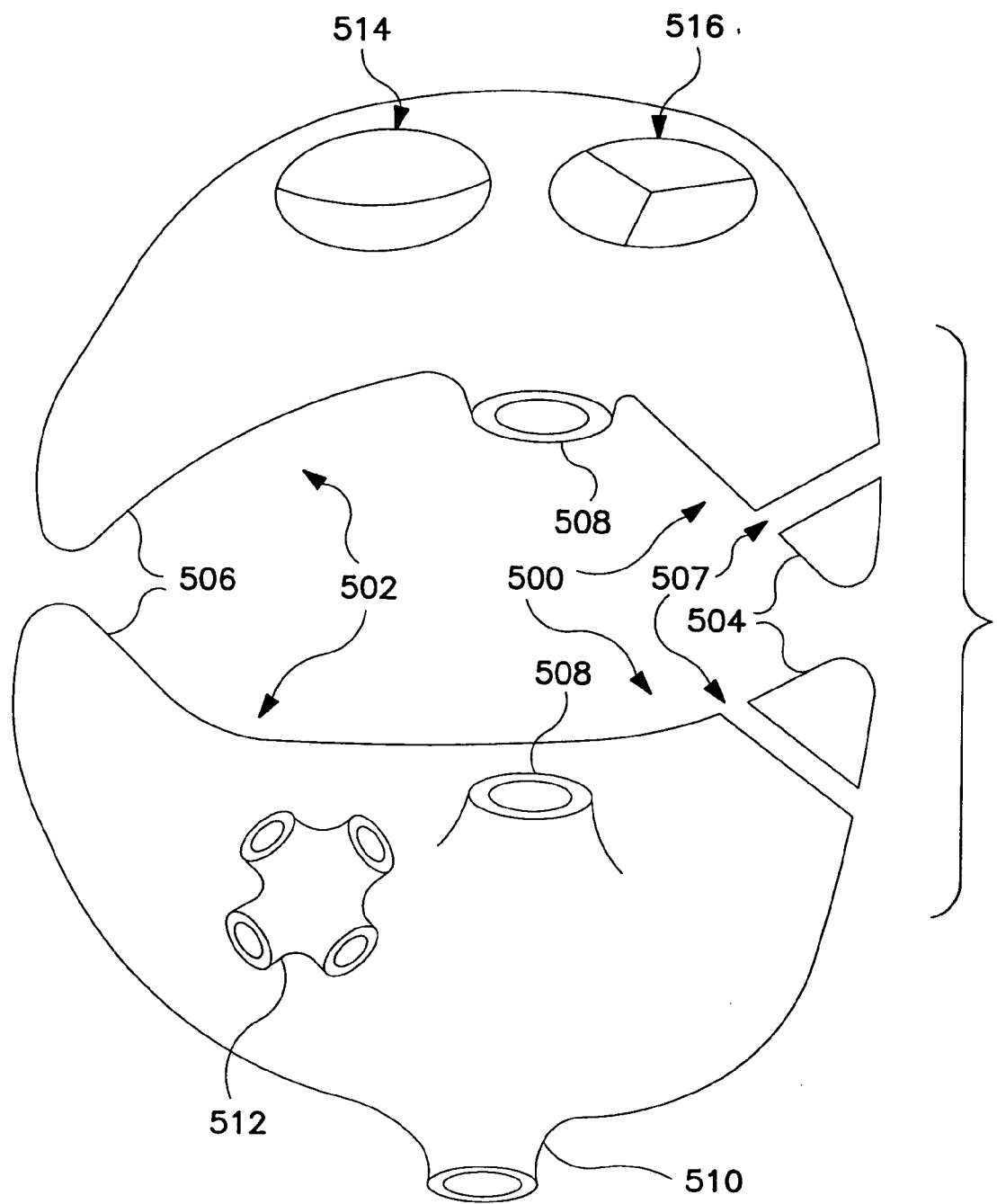

For purposes of understanding the basic method of the present invention as illustrated, it should be assumed that the operation is undertaken as an open chest operation, with the heart stopped and the patient on full bypass. Modifications to the procedure, in case of a limited access, stopped heart procedure and/or a limited access, beating heart procedure, are also generally described. FIG. 9B illustrates the first step of the procedure, comprising removal of the right atrial appendage 504. Right atrial appendage 504 is removed by means of an incision 507, which may be made by means of a scalpel or scissors. In a context of a closed chest procedure on either a beating or a stopped heart, a thoracoscopic tool may be substituted, preferably one capable of simultaneously cutting and stapling the remnant of the right atrial appendage.

Figure 9C:
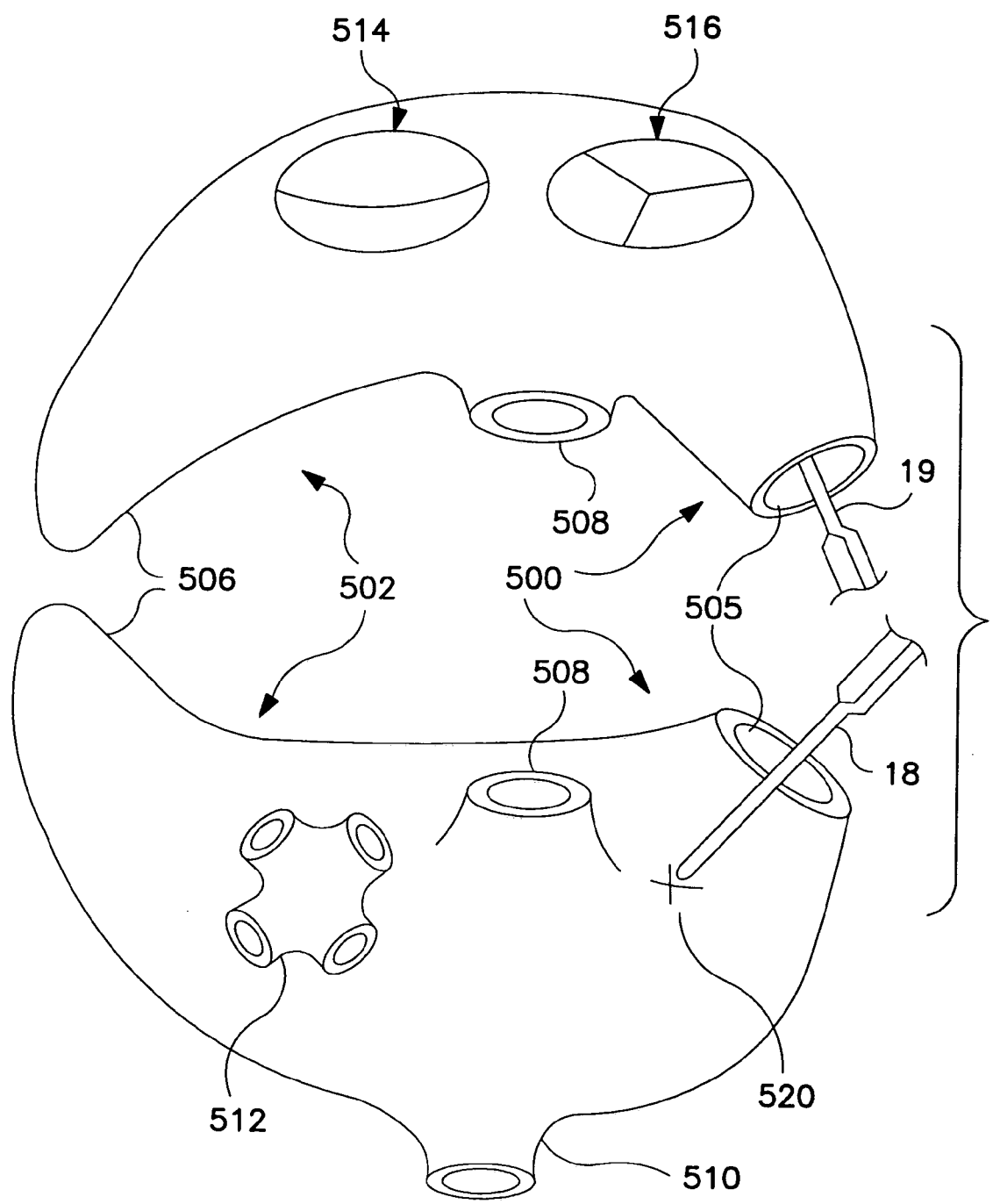

FIG. 9C illustrates the second step of the procedure, as performed using an open chest approach. During the second step, the electrosurgical hemostat of the present invention, with the jaws in the straight configuration as illustrated FIG. 1A, with one jaw 19 of the hemostat inserted into the right atrium through the opening left by removal of the right atrial appendage and the other jaw 18 arranged along the exterior surface of the heart. Jaws 18 and 19 are inserted until they extend to a point 520 located approximately at the mid point of the right atrium, approximately 5 centimeters from the opening 505 left by removal of the right atrial appendage. The jaws 18 and 19 are compressed and RF energy is applied between the electrodes located in jaws 18 and 19 to create an elongated lesion, extending through the tissue of the right atrial wall, to provide a block against passage of depolarization waves there across. For purposes of the following drawings, the placement of various hemostats will be described, but now specifically illustrated. Instead, the lesions to be produced by the hemostats will be illustrated by means of beaded lines, so that their interconnection and their relationship to the structures of the left and right atria 502, 500, may be understood. It should be understood that the hemostats are to be placed with their jaws extending along the lesions as illustrated, unless otherwise specified.

In closed chest, limited access procedures, it is anticipated that the lesion produced may be made by inserting the jaw of an electrosurgical hemostat as illustrated in conjunction FIG. 1A, but having a sharpened tip as illustrated in FIG. 1B, directly through the heart wall at point 520, and the jaws advanced to the sealed remnant of the removal of the right atrial appendage to define a corresponding lesion.

Figure 9D:
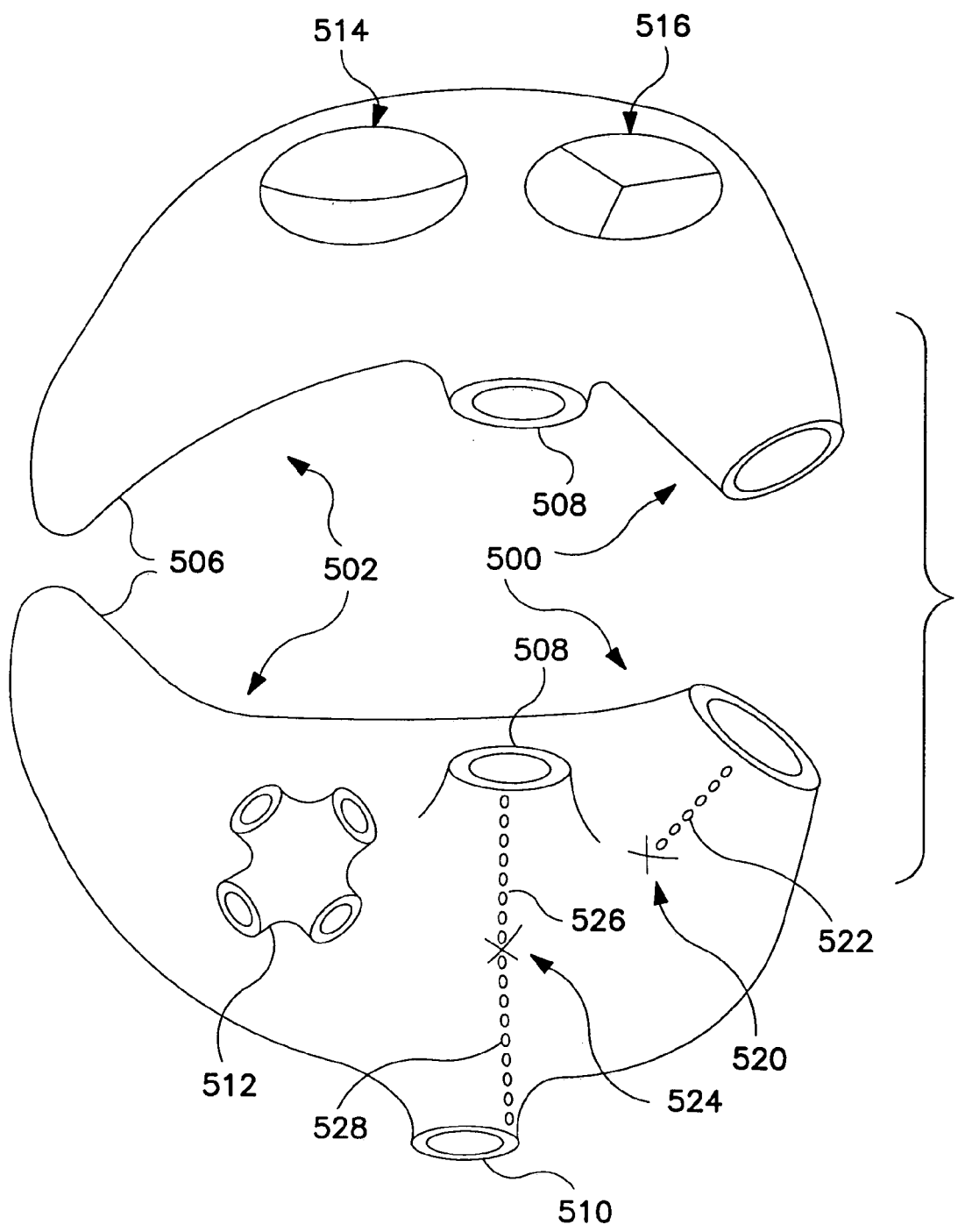

FIG. 9D illustrates the next step in the procedure and also illustrates lesion 522 produced by the application of the electrosurgical hemostat with jaws retaining the straight configuration as illustrated in FIG. 1A. Lesion 522 corresponds generally to the incision illustrated at step A1 as described in the Doty reference. At 524, a local access incision is cut, at a point approximately midway between the inferior vena cava and superior vena cava (510, 508). Lesions 526 and 528, extending from access incision 524 to the superior and inferior vena cava, respectively, are produced by inserting one jaw of a hemostat as illustrated in FIG. 1A through the access incision 524 and arranging the jaws of the hemostat to extend on either side of atrial tissue from the incision 524 to the superior vena cava and inferior vena cava, respectively. Alternatively, the jaws of the hemostat may be configured as illustrated in FIG. 3. The lesions 528 and 526 so produced correspond to the incisions illustrated at step B as described in the Doty reference. In more limited access surgeries, hemostats having sharpened jaws as illustrated in FIG. 1B might be employed, with the sharpened tip of a jaw employed to create the access incision 524.

Figure 9E:
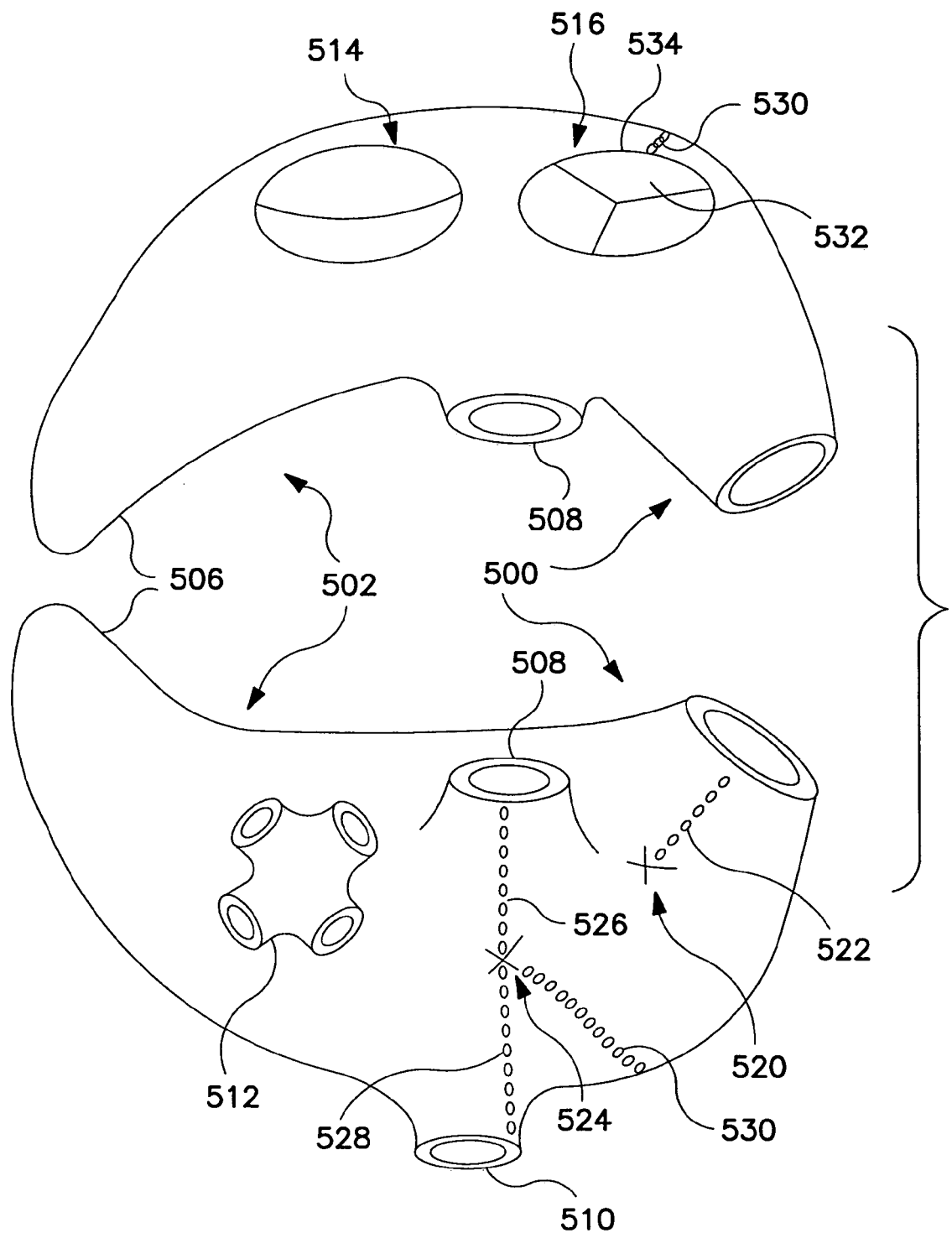

FIG. 9E illustrates the next step in the procedure. In this step, one jaw of the hemostat, having a configuration as illustrated in FIG. 1A or FIG. 3 is inserted through access incision 524, and the jaws are arranged along either side of the atrial wall to create lesion 530, extending to the annulus of tricuspid valve 516, terminating at a point 534 approximately at the center of the posterior leaflet 532. This lesion should extend as close as possible to the tricuspid annulus. This lesion corresponds generally to the incision illustrated at steps D and E as described in the Doty reference. Optionally, cryo-ablation may be performed at the tricuspid annulus at the terminus of lesion 530, by means of a cryo-probe inserted through the opening 505 in the remnant of the right atrial appendage. Cryo-ablation corresponds generally to that illustrated at step F as described in the Doty reference. In more limited access surgeries, the cryo-probe might be inserted through access lesion 524 or might be inserted transvenously.

Figure 9F:
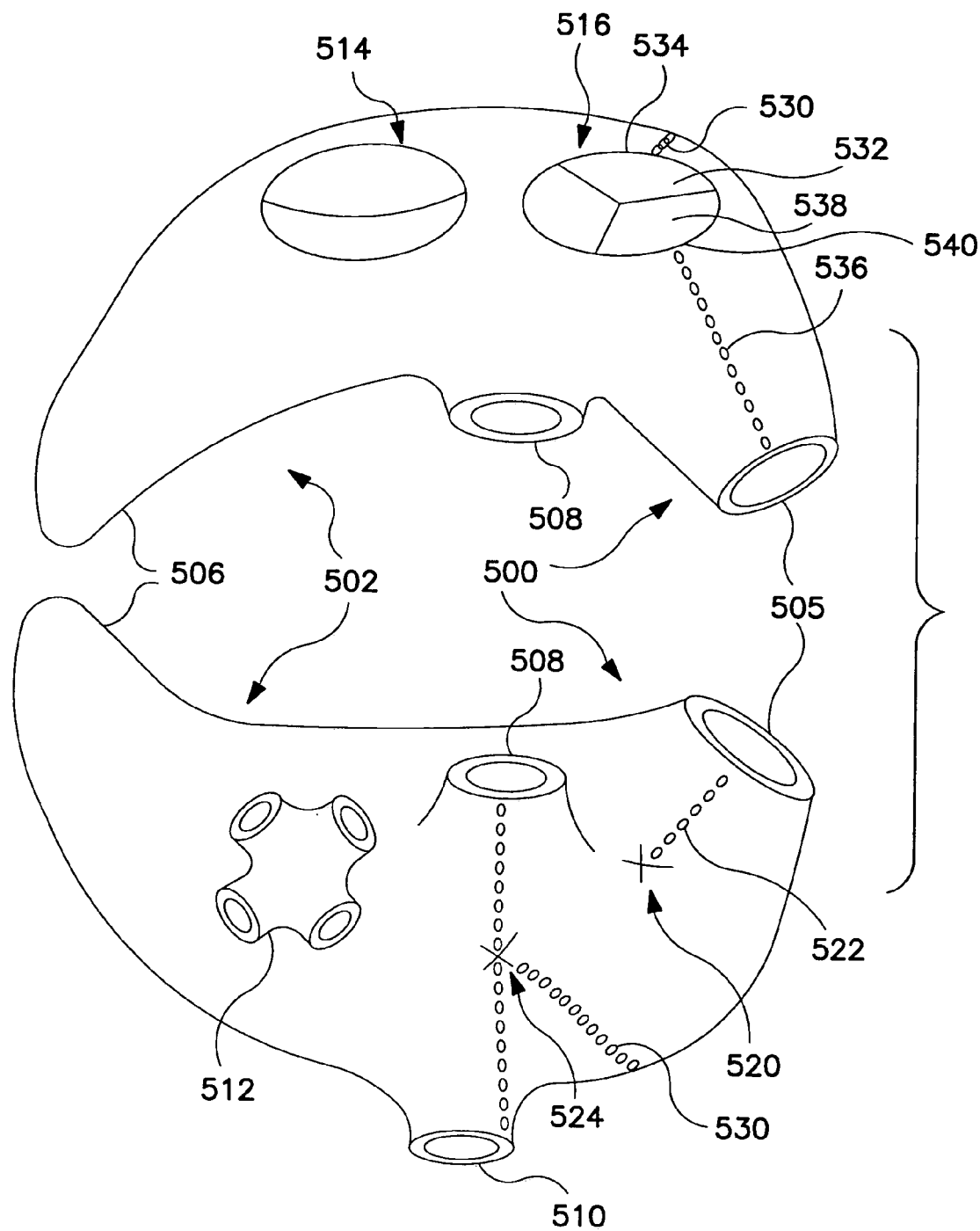

FIG. 9F illustrates the next step of the procedure. In FIG. 9F, lesion 536 is created using the distal portion of the jaws of a hemostat configured as in FIG. 1A. One jaw of the hemostat is inserted through the opening 505 in the remnant of the right atrial appendage, and the jaws are arranged to extend along either the right atrial wall to the annulus of the tricuspid valve 516 at the midpoint of the anterior leaflet 538. This lesion corresponds generally to the incision illustrated at steps H and I as described in the Doty reference. Care must be taken during this step to avoid the right coronary artery. Optionally, cryo-ablation may be applied at the tricuspid annulus at point 540, at the termination of lesion 536. Again, cryo-ablation may be provided by means of a cryo-probe inserted via the opening 505 in the remnant of the right atrial appendage, through access lesion 524, or, alternatively be means of a cryo-probe inserted transvenously. Cryo-ablation corresponds generally to that illustrated at step J as described in the Doty reference.

Figure 9G:
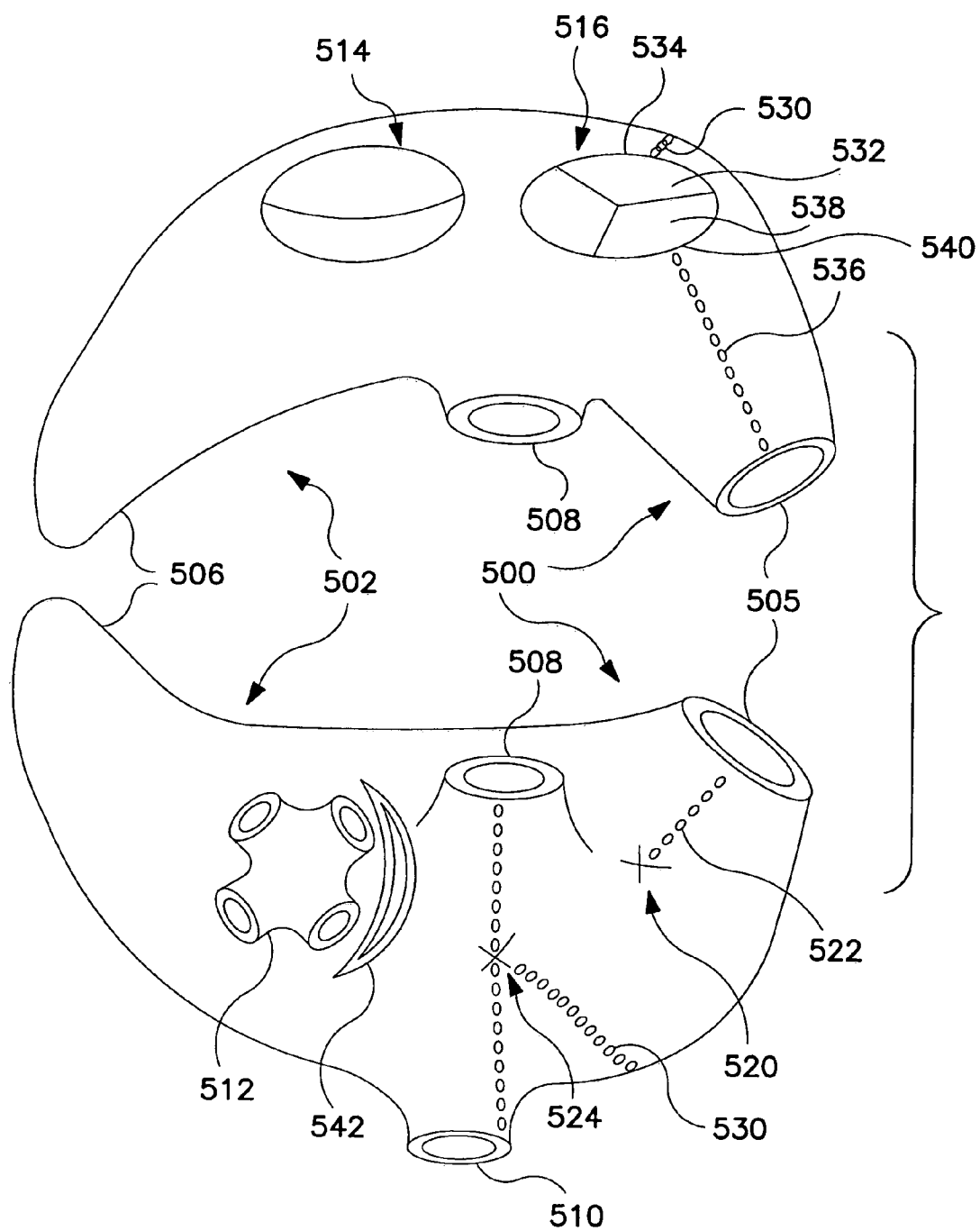

FIG. 9G illustrates the next step of the procedure which is the creation of an incision 542 extending through the left atrial wall, posterior to the inter atrial groove, near the orifices of the right pulmonary veins. In an open chest procedure, incision 542 may be made conventionally by means of scissors or a scalpel. Incision 542 corresponds to the incision illustrated at step K as described in the Doty reference. In more limited access surgeries, incision 542 might be replaced by a simple access incision made by means of the sharpened tip of one of the jaws of the hemostats used to create the lesions surrounding the orifices of the pulmonary veins, as discussed below.

Figure 9H:
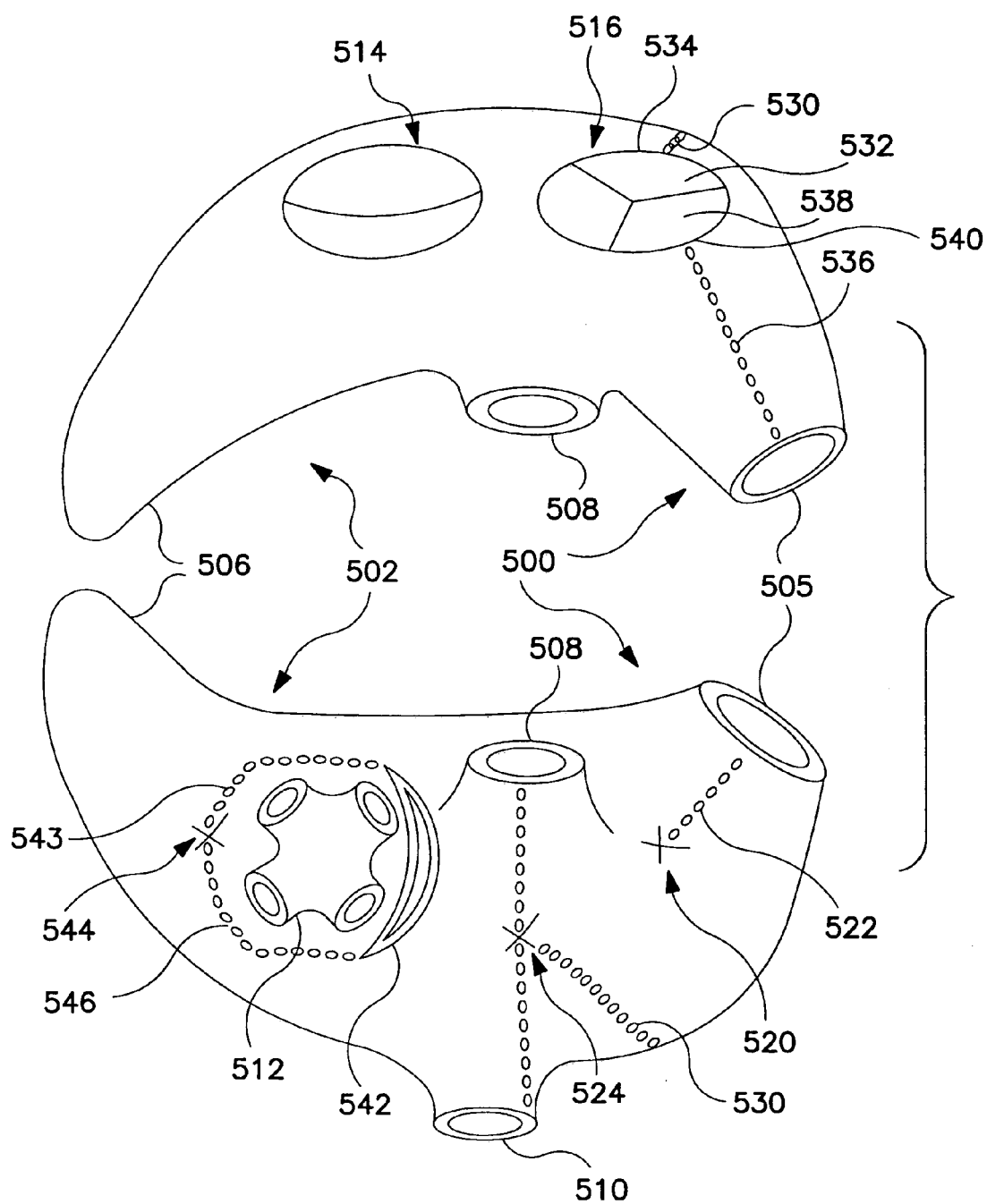

FIG. 9H illustrates the next step of the procedure, which is the creation of lesions 543 and 546. Lesions 543 and 546 may be accomplished by insertion of the hemostat having jaws re-shaped to the curved configuration as illustrated in FIG. 5, reversing the orientation of the hemostat between lesions, to create two curved lesions extending around the base of the pulmonary veins 512 and meeting at a point 544, to complete the lesion path. Lesions 543 and 546 correspond generally to the incisions illustrated at steps L and N as described in the Doty reference. In an alternative procedure, lesions approximating the incisions illustrated at steps L and N may be produced by compressing the atrial wall tissue adjacent the bases of the left pulmonary veins between jaws of the hemostat illustrated in FIG. 4A or 5A applied epicardially to produce a lesion encircling the bases of the left pulmonary veins and repeating the procedure to correspondingly produce a lesion encircling the bases of the right pulmonary veins.

Figure 9I:
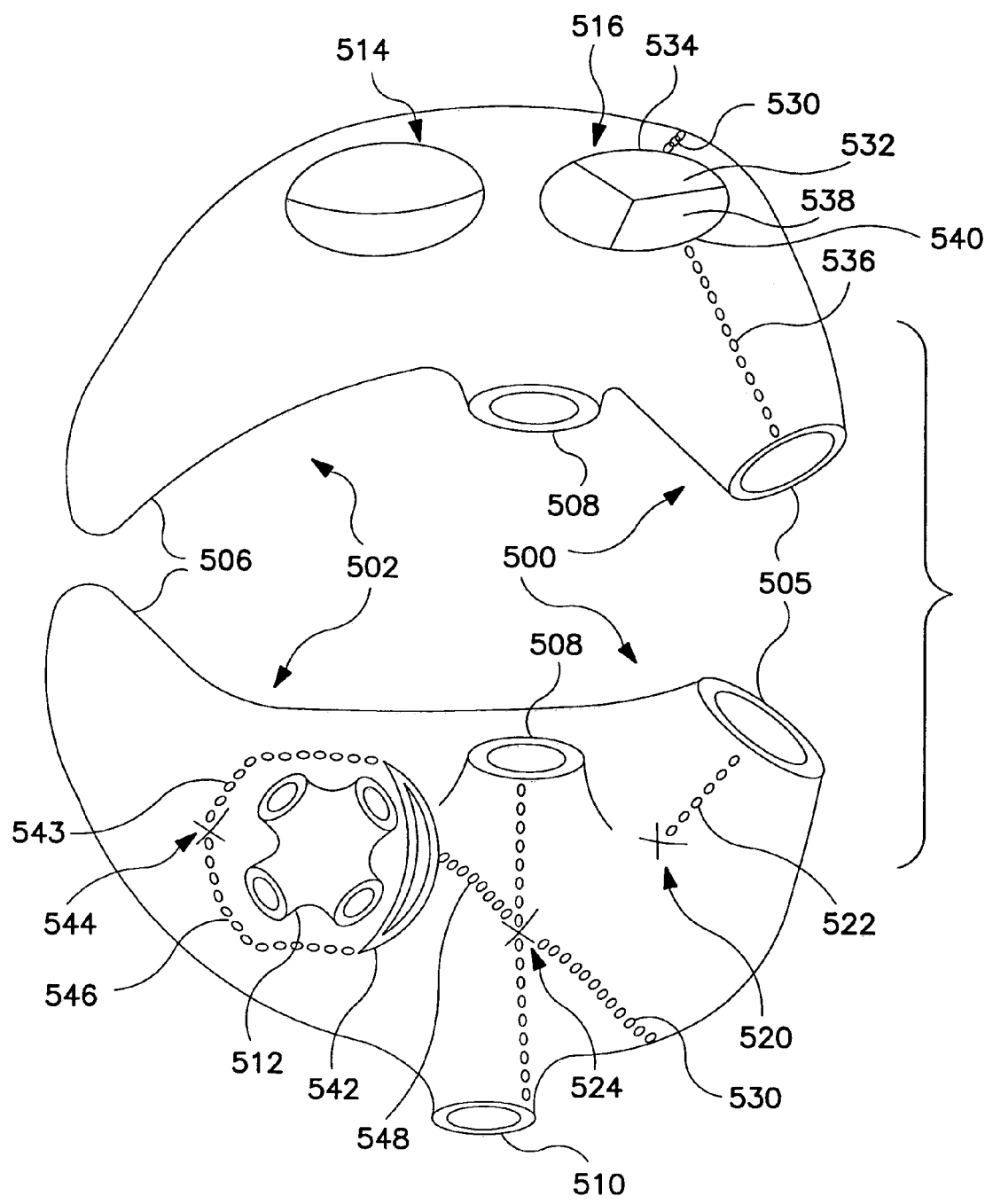

FIG. 9I illustrates the next step of the procedure, in which the hemostat is reshaped to display the more sharply curved configuration as illustrated in FIG. 4 is employed to create lesion 548. Lesion 548 is created by inserting one jaw of the hemostat, into incision 542, the other into access incision 524, and compressing the atrial septum therebetween. The jaws are arranged so that they define a curved lesion extending along the atrial septum, extending to a point above the fossa ovalis, near but not into the tendon of Todaro. As the atrial septum is not visible in FIG. 9I, lesion 544 should be understood to correspond to the incision illustrated at step M as described in the Doty reference.

Figure 9J:
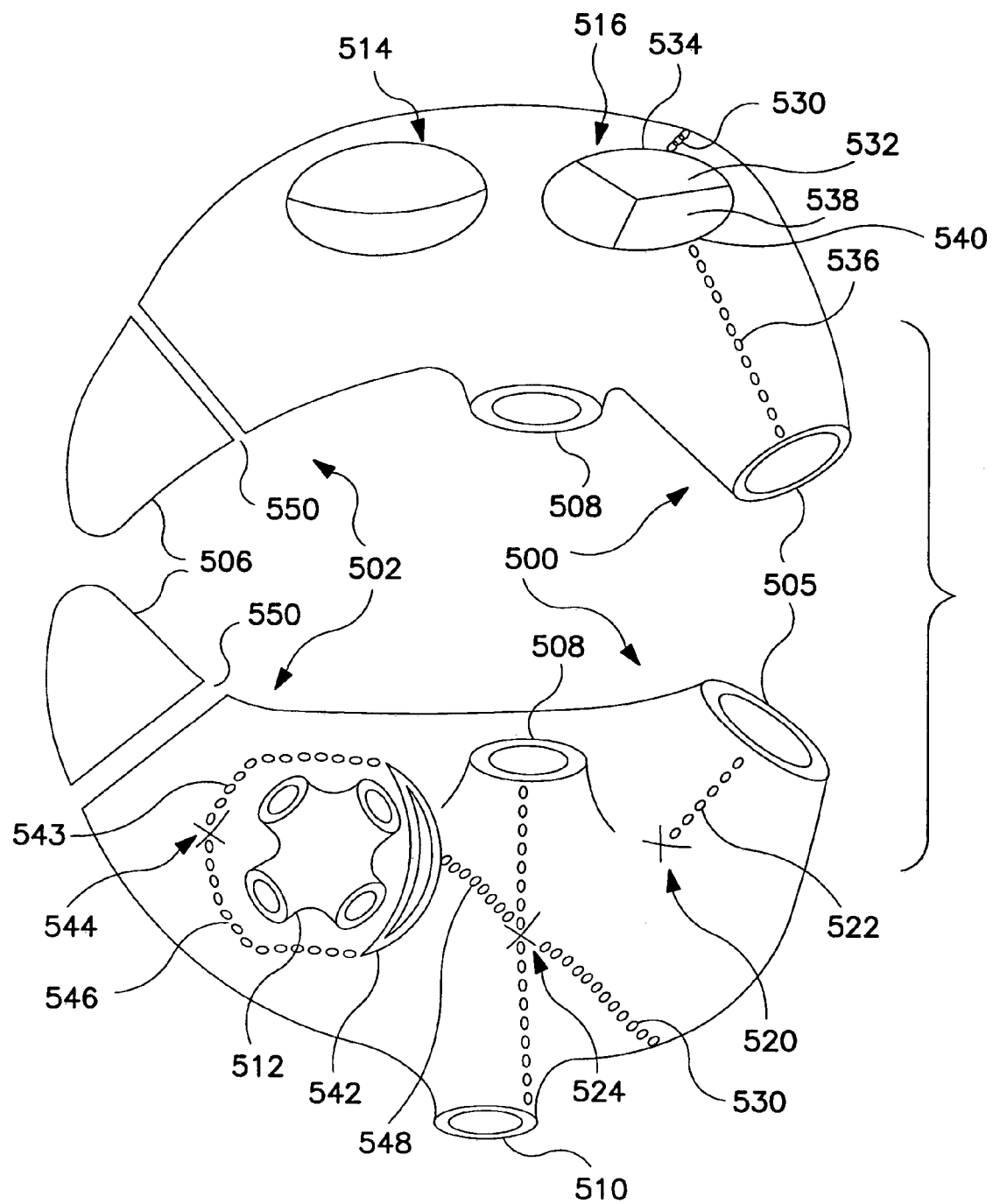

FIG. 9J illustrates the next step in the procedure, comprising the removal of left atrial appendage 506 by means of an incision 550. In open chest procedures, this incision might be made by means of a scissors or scalpel. In more limited access surgeries, this incision might be made by means of a thoracoscopically introduced, preferably one capable of simultaneously cutting and stapling the remnant of the right atrial appendage.

Figure 9K:
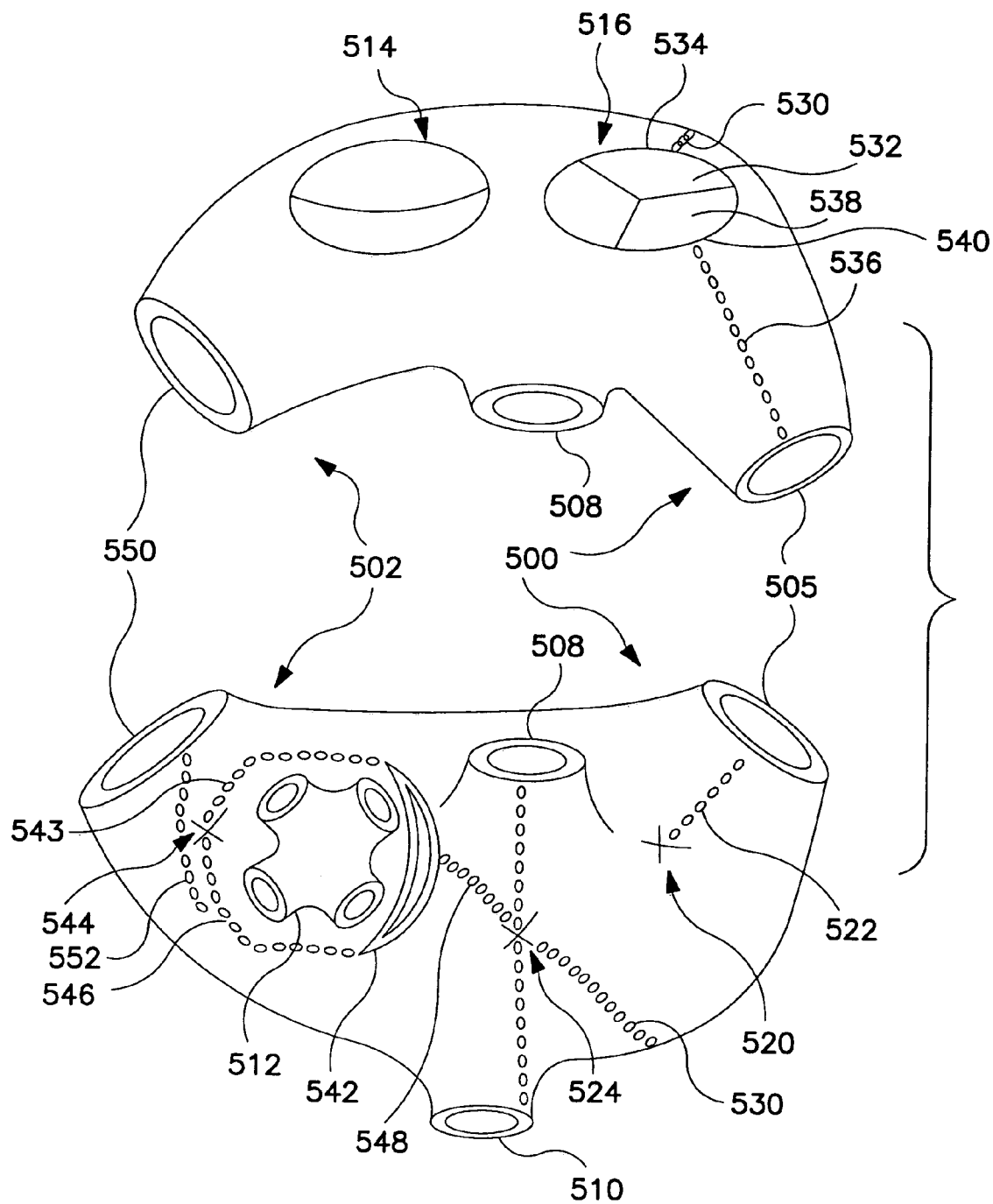
Figure 9L:
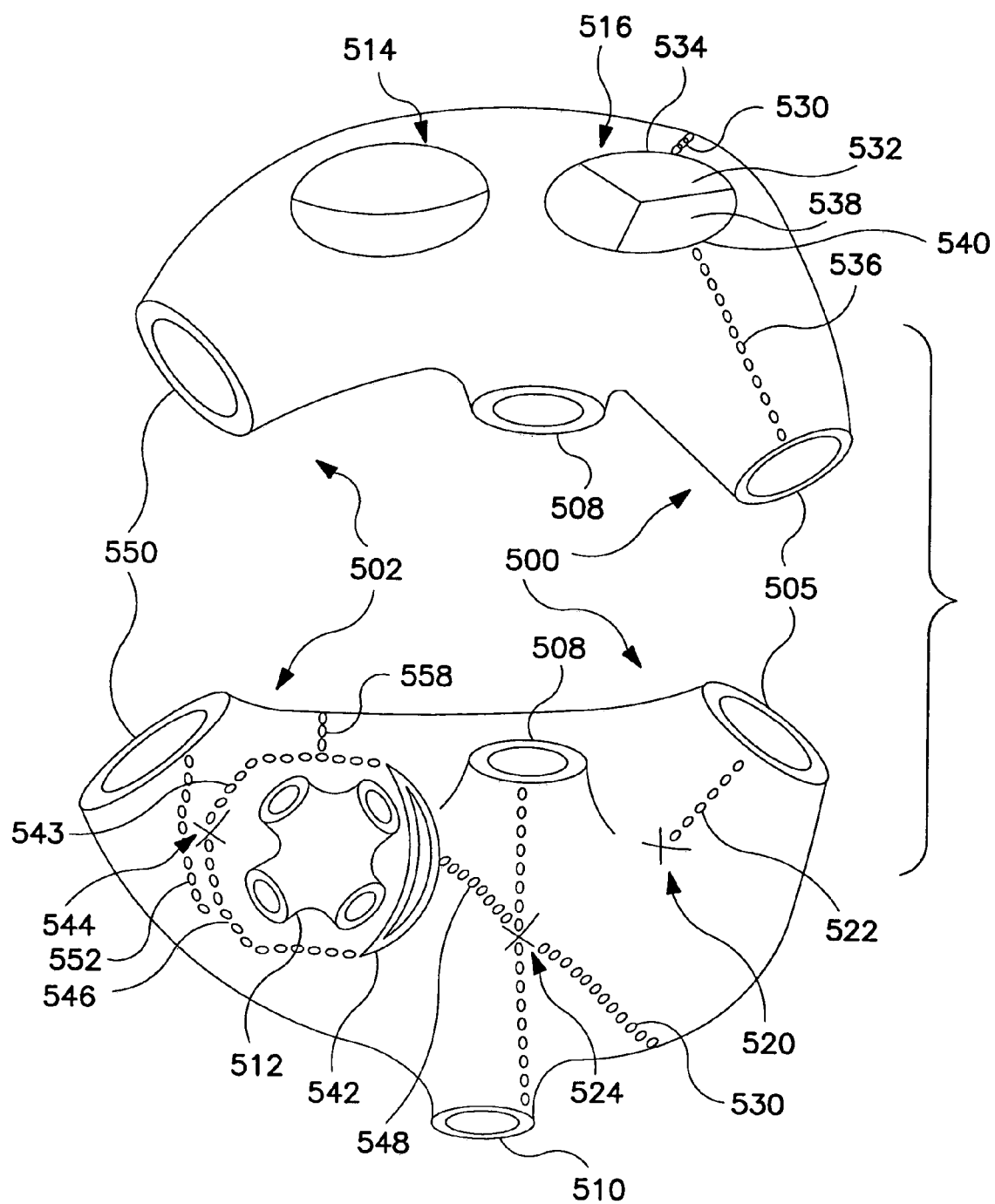

FIG. 9K illustrates the next step of the procedure, comprising the creation of lesion 552. Lesion 552 may be created using the hemostat reshaped to display the more gently curved configuration illustrated in FIG. 5 to create a curved lesion departing from lesion 546 and extending to the opening 550 in the right atrial appendage. As with lesions 543 and 546, the lesion may be produced by inserting one jaw of the hemostat through the incision 542, and compressing the left atrial wall between the jaws of the hemostat. Lesion 552 might also be performed prior to removal of the left atrial appendage, in conjunction with creation of lesions 543 and 546. In some embodiments of the invention, lesion 542 might be replaced by a simple incision extending from the opening 550 of the remnant of the left atrial appendage, and then later repaired by suture FIG. 9L illustrates the next step of the procedure, comprising the creation of lesion 558. Lesion 558 is created using the hemostat configured as in FIG. 5, one jaw being inserted through incision 542 and compressing the left atrial wall between the jaws of the hemostat to create a lesion extending from lesion 543 to the mid point 560 of the annulus of the posterior mitral valve. Lesion 558 corresponds to the incision illustrated at step S as described in the Doty reference. Care must be exercised during this incision to prevent damage to the circumflex artery and the coronary sinus. Optionally cryo-ablation may be provided at the mid-point 560 of the posterior mitral valve annulus, by means of a cyro-probe introduced through the opening 550 through the remnant of a left atrial appendage, or through incision 542. In more limited access surgeries, cryo ablation may be provided by means of transvenous cyro-ablation catheter. Cryo-ablation corresponds generally to that illustrated at step J as described in the Doty reference.

Figure 9M:
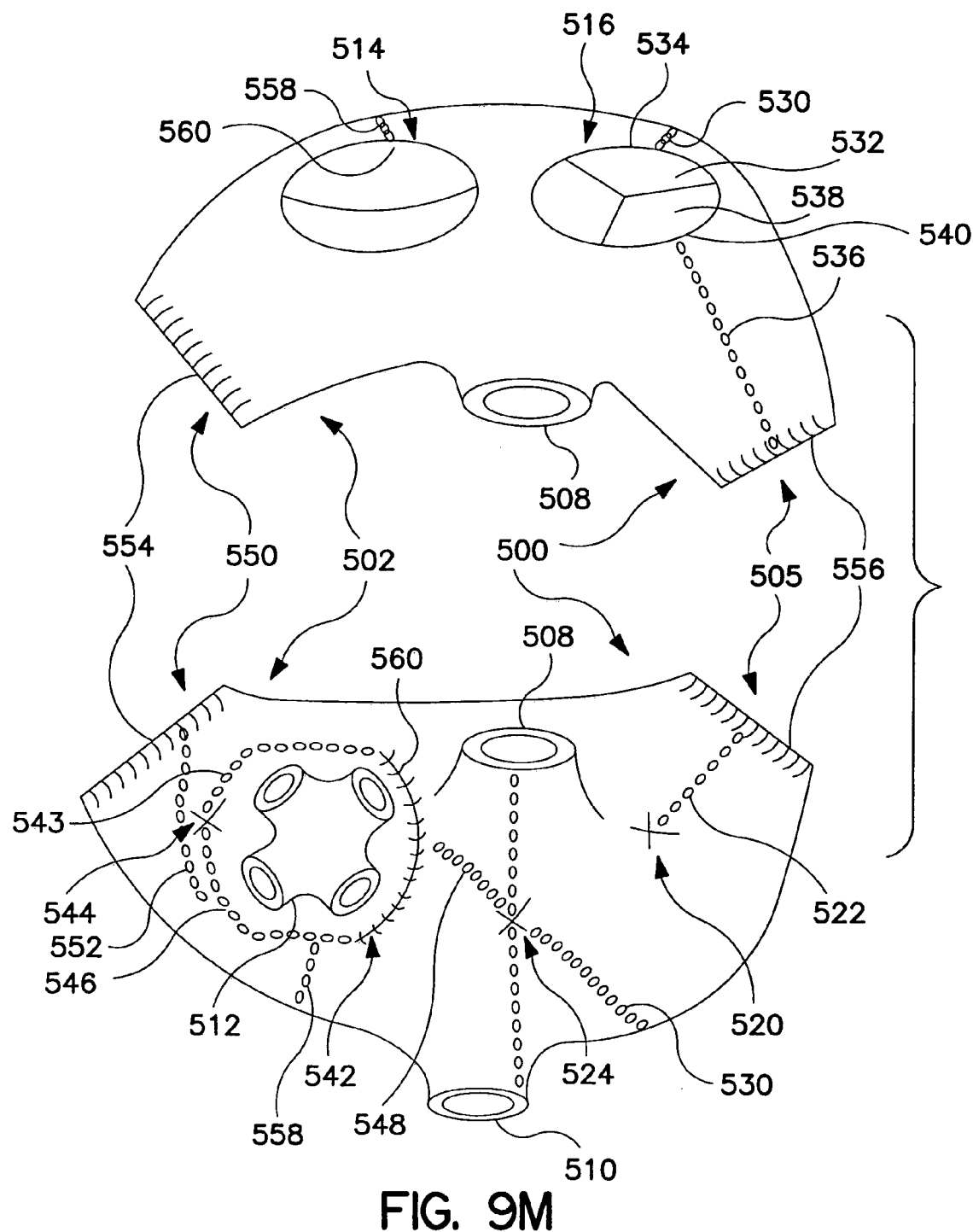

FIG. 9M illustrates the final steps of the procedure, comprising closing of the openings 505 and 550 into the remnants of the right and left atrial appendages, respectively, by means of sutures 554 and 556. As noted above, in the event that thoracoscopic surgical implements are employed, these openings may have previously been closed in conjunction with their creation, by means of staples, or otherwise, by means of thoracoscopic surgical tools. In addition, incision 542 is shown as closed by means of sutures 560 as discussed above, in some embodiments, incision 542 may have been replaced by simple puncture incision, which might be closed by means of staple, sutures, or otherwise, applied thoracoscopically. Access in incision 524 is similarly closed at this time.

The hemostat as illustrated in FIGS. 1A through 5, discussed above, has the general configuration of a conventional hemostat, as would be employed in the context of an open chest procedure. In the event that the procedure is adapted to a thoracoscopic procedure, similarly configured hemostat jaws may be employed on a thoracoscopically introduced instrument to create the various lesion patterns. Modifications to the specific configurations of the disclosed hemostat may be desirable in conjunction with adapting the hemostat to thoracoscopic use or in conjunction with adapting the hemostat set to other versions of the Maze or Maze type procedures or to procedures performed elsewhere on the heart or other organs. Such modifications are believed to be within the scope of the invention.

While the hemostat disclosed in the present application is preferably provided with R-F electrodes to create elongated lesions, it is believed the invention may also usefully be practiced in conjunction with hemostats employing microwave, heat, cyro-ablation or other ablative techniques to create the various lesions provided by the method. Further, while the hemostats disclosed in the present application are provided with a single elongated electrode extending along each jaw, embodiments in which multiple electrodes arrayed along each jaw are employed are also believed useful in practicing the invention. Further yet, as noted above, the present invention is also believed useful in the context ablation devices employing only a single elongated, electrode or a single series of electrodes.

Therefore, the above disclosure should be considered as exemplary, rather than limiting, with regard to the following claims.

In conjunction with the above specification, we claim:

What is claimed is:

1. A method of ablation to provide a desired set of lesions, comprising:

(a) providing an ablation apparatus having a pair of jaw components, each jaw component having an elongated shapeable section, each elongated shapeable section having one or more ablation elements extending along its length for applying ablation energy along the shapeable section, at least one jaw component having a sharpened distal tip;

(b) shaping the shapeable section of each jaw component to display a desired configuration corresponding to one of the desired lesions;

(c) piercing an atrial wall with the sharpened distal tip;

(d) employing the ablation apparatus to create the desired lesion;

(e) thereafter reshaping the shapeable section of each jaw component to display a desired configuration corresponding to another of the desired lesions;

(f) repeating steps b, c, d and e as necessary provide the desired set of lesions.

2. A method as in claim 1, wherein shaping the shapeable section of each jaw component comprises manually bending the shapeable section.

3. A method as in claim 1, wherein shaping the shapeable section of each jaw component comprises bending the shapeable section using a bending fixture.

4. A method as in claim 3, wherein the bending fixture retains the jaws in a parallel arrangement.

5. A method as in claim 1, wherein shaping the shapeable section of each jaw component comprises selecting a bending fixture from among a set of fixtures and bending the shapeable section using the selected bending fixture.

6. A method as in claim 1, wherein shaping the shapeable section of each jaw component comprises configuring a bending fixture to define the desired configuration and bending the shapeable section using the configured bending fixture.

7. A method as in claim 1, wherein providing the ablation apparatus comprises selecting an ablation apparatus having a generally straight memorized configuration.

8. A method as in claim 1, wherein selecting the ablation apparatus comprises providing an ablation apparatus having a memorized configuration corresponding to a desired lesion.

9. A method as in claim 8, comprising employing the ablation apparatus in its memorized configuration to create the desired lesion.

10. A method as in claim 1, wherein reshaping the shapeable section of each jaw component comprises heating the shapeable section.

11. A method as in claim 10, wherein reshaping the shapeable section of each jaw component comprises heating the shapeable section by means of a heater mounted to the shapeable section.

12. A method as in claim 1, wherein the shapeable section of each jaw component comprises a shape memory material.

13. A method as in claim 1, wherein the ablation elements are electrodes.

14. A method as in claim 1, wherein the shapeable section of each jaw component comprises shapeable material.

15. A system for providing a desired set of lesions, comprising:

(a) an ablation apparatus having a pair of jaw components, each jaw component having an elongated shapeable section, each elongated shapeable section having one or more ablation elements extending along its length for applying ablation energy along the shapeable section, each shapeable section comprising a member of shapeable material, at least one jaw component having a sharpened distal tip for piercing atrial wall tissue; and (b) fixturing apparatus for shaping the shapeable section of each jaw component to display multiple, predetermined configurations corresponding to the desired lesions.

16. A system as in claim 15, wherein the fixturing apparatus comprises a set of fixtures defining curvatures corresponding to the desired configurations.

17. A system as in claim 15, wherein the fixturing apparatus comprises a configurable fixture capable of defining multiple curvatures corresponding to the desired configurations.

18. A system as in claim 15, wherein the shapeable section of each jaw component has a generally straight memorized configuration.

19. A system as in claim 15, wherein the shapeable section of each jaw component has a memorized configuration corresponding to a desired lesion.

20. A system as in claim 15, wherein a heater is located on the shapeable section of each jaw component.

21. A system as in claim 15, wherein the fixturing apparatus retains the jaws in a parallel arrangement.

22. A system as in claim 15, wherein the ablation elements are electrodes.

23. A system as in claim 15, wherein the shapeable section of each jaw component comprises shapeable material.

24. A system for providing a desired set of lesions, comprising:

an ablation apparatus comprising an electrosurgical hemostat having elongated shapeable jaws, each jaw carrying means for applying ablation energy along the shapeable section, the shapeable section comprising a member of shapeable material, and a sharpened distal tip for piercing atrial wall tissue; and a bending fixture for shaping the shapeable section of each jaw to display multiple, predetermined configurations corresponding to the desired lesions, wherein the bending fixture comprises means for retaining the jaws in a parallel arrangement.

25. A system for providing a desired set of lesions, comprising:

an ablation apparatus comprising an electrosurgical hemostat having elongated shapeable jaws having electrodes extending along their length for applying ablation energy along the shapeable section, the shapeable section comprising a member of shapeable material, and a sharpened distal tip for piercing atrial wall tissue; and fixturing means for shaping the shapeable section to display multiple, predetermined configurations corresponding to the desired lesions.

26. A system as in claim 25, further comprising means for delivery of conductive fluid along the length of the electrodes.

* * * * *